(12) United States Patent
Pilletere et al.

(10) Patent No.: US 11,357,542 B2
(45) Date of Patent: Jun. 14, 2022

(54) VALVE ASSEMBLY AND RETAINER FOR SURGICAL ACCESS ASSEMBLY

(71) Applicant: Covidien LP, Mansfield, MA (US)

(72) Inventors: Roy Pilletere, North Haven, CT (US); Jacob Baril, Norwalk, CT (US); Garrett Ebersole, Hamden, CT (US); Matthew Dinino, Newington, CT (US); Justin Thomas, New Haven, CT (US); Eric Brown, Haddam, CT (US); Nicolette LaPierre, Windsor Locks, CT (US)

(73) Assignee: Covidien LP, Mansfield, MA (US)

( * ) Notice: Subject to any disclaimer, the term of this patent is extended or adjusted under 35 U.S.C. 154(b) by 198 days.

(21) Appl. No.: 16/448,654

(22) Filed: Jun. 21, 2019

(65) Prior Publication Data

US 2020/0397469 A1 Dec. 24, 2020

(51) Int. Cl.
*A61B 17/34* (2006.01)
*F16K 13/02* (2006.01)
*F16K 99/00* (2006.01)

(52) U.S. Cl.
CPC .......... *A61B 17/3423* (2013.01); *F16K 13/02* (2013.01); *A61B 2017/345* (2013.01); *A61B 2017/3441* (2013.01); *A61B 2017/3445* (2013.01); *F16K 2099/0086* (2013.01)

(58) Field of Classification Search
CPC ............ A61B 17/3423; A61B 17/3462; A61B 2017/3441; A61B 2017/3445; A61B 2017/345; A61B 2017/3464; A61B 2017/3425–3429; A61B 2017/3447; A61B 2017/3449; A61B 2017/3452; A61B 2017/3466; F16K 13/02; F16K 2099/0086; F16K 2099/0088

USPC ......................................................... 600/184
See application file for complete search history.

(56) References Cited

U.S. PATENT DOCUMENTS

| | | | |
|---|---|---|---|
| 3,189,223 A | 6/1965 | Mackal | |
| 3,206,784 A | 9/1965 | Linenfelser | |
| 3,253,594 A | 5/1966 | Matthews et al. | |
| 3,258,809 A | 7/1966 | Harvey | |
| 3,261,350 A | 7/1966 | Wallace | |
| 3,402,710 A | 9/1968 | Paleschuck | |

(Continued)

FOREIGN PATENT DOCUMENTS

| | | |
|---|---|---|
| AU | 2005202133 A1 | 12/2006 |
| CA | 2702419 A1 | 11/2010 |

(Continued)

OTHER PUBLICATIONS

Extended European Search Report dated Sep. 4, 2020 issued in corresponding EP Appln. No 20181290.6.

*Primary Examiner* — Tuan V Nguyen
(74) *Attorney, Agent, or Firm* — Carter, DeLuca & Farrell LLP

(57) ABSTRACT

A surgical access assembly includes a cannula, a valve housing attached to the cannula, and a valve assembly positioned in the valve housing. The valve assembly includes a centering mechanism with a hoop and fingers, a ring with a flange at one end of the ring, a retainer having first and second discs, a guard having a frame and flaps attached to the frame, and a seal with petals attached to a support. The guard is at least partially disposed in the first disc and the seal is at least partially disposed in the second disc.

13 Claims, 12 Drawing Sheets

(56) References Cited

U.S. PATENT DOCUMENTS

| | | |
|---|---|---|
| 3,495,586 A | 2/1970 | Regenbogen |
| 3,840,145 A | 10/1974 | Almanza |
| 4,016,884 A | 4/1977 | Kwan-Gett |
| 4,112,932 A | 9/1978 | Chiulli |
| 4,114,668 A | 9/1978 | Hickey |
| 4,183,357 A | 1/1980 | Bentley et al. |
| 4,281,646 A | 8/1981 | Kinoshita |
| 4,294,234 A | 10/1981 | Matsuo |
| 4,356,826 A | 11/1982 | Kubota |
| 4,359,049 A | 11/1982 | Redl et al. |
| 4,402,683 A | 9/1983 | Kopman |
| 4,447,237 A | 5/1984 | Frisch et al. |
| 4,475,548 A | 10/1984 | Muto |
| 4,519,908 A | 5/1985 | Woodruff |
| 4,610,665 A | 9/1986 | Matsumoto et al. |
| 4,619,643 A | 10/1986 | Bai |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,874,368 A | 10/1989 | Miller et al. |
| 4,919,113 A | 4/1990 | Sakamoto et al. |
| 4,941,872 A | 7/1990 | Felix et al. |
| 4,978,336 A | 12/1990 | Capozzi et al. |
| 4,979,942 A | 12/1990 | Wolf et al. |
| 4,984,564 A | 1/1991 | Yuen |
| 5,002,557 A | 3/1991 | Hasson |
| 5,015,228 A | 5/1991 | Columbus et al. |
| 5,041,095 A | 8/1991 | Littrell |
| 5,073,169 A | 12/1991 | Raiken |
| 5,082,005 A | 1/1992 | Kaldany |
| 5,104,389 A | 4/1992 | Deem et al. |
| 5,122,122 A | 6/1992 | Allgood |
| 5,127,626 A | 7/1992 | Hilal et al. |
| 5,127,909 A | 7/1992 | Shichman |
| 5,159,921 A | 11/1992 | Hoover |
| 5,176,697 A | 1/1993 | Hasson et al. |
| 5,180,376 A | 1/1993 | Fischell |
| 5,183,471 A | 2/1993 | Wilk |
| 5,192,301 A | 3/1993 | Kamiya et al. |
| 5,203,767 A | 4/1993 | Cloyd |
| 5,207,213 A | 5/1993 | Auhll et al. |
| 5,207,656 A | 5/1993 | Kranys |
| 5,209,741 A | 5/1993 | Spaeth |
| 5,209,754 A | 5/1993 | Ahluwalia |
| 5,217,466 A | 6/1993 | Hasson |
| 5,226,890 A | 7/1993 | Ianniruberto et al. |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,263,927 A | 11/1993 | Shlain |
| 5,263,939 A | 11/1993 | Wortrich |
| 5,269,754 A | 12/1993 | Rydell |
| 5,269,772 A | 12/1993 | Wilk |
| 5,271,380 A | 12/1993 | Riek et al. |
| 5,274,874 A | 1/1994 | Cercone et al. |
| 5,290,245 A | 3/1994 | Dennis |
| 5,290,249 A | 3/1994 | Foster et al. |
| 5,307,803 A | 5/1994 | Matsuura et al. |
| 5,308,336 A | 5/1994 | Hart et al. |
| 5,312,351 A | 5/1994 | Gerrone |
| 5,312,391 A | 5/1994 | Wilk |
| 5,312,417 A | 5/1994 | Wilk |
| 5,313,934 A | 5/1994 | Wiita et al. |
| 5,314,417 A | 5/1994 | Stephens et al. |
| 5,318,516 A | 6/1994 | Cosmescu |
| 5,330,486 A | 7/1994 | Wilk |
| 5,330,497 A | 7/1994 | Freitas et al. |
| 5,334,143 A | 8/1994 | Carroll |
| 5,334,150 A | 8/1994 | Kaali |
| 5,336,169 A | 8/1994 | Divilio et al. |
| 5,336,203 A | 8/1994 | Goldhardt et al. |
| 5,337,730 A | 8/1994 | Maguire |
| 5,337,800 A | 8/1994 | Cook |
| 5,337,937 A | 8/1994 | Remiszewski et al. |
| 5,338,313 A | 8/1994 | Mollenauer et al. |
| 5,342,315 A | 8/1994 | Rowe et al. |
| 5,345,927 A | 9/1994 | Bonutti |
| 5,346,459 A | 9/1994 | Allen |
| 5,354,302 A | 10/1994 | Ko |
| 5,358,488 A | 10/1994 | Suriyapa |
| 5,360,417 A | 11/1994 | Gravener et al. |
| 5,366,478 A | 11/1994 | Brinkerhoff et al. |
| 5,368,563 A | 11/1994 | Lonneman et al. |
| 5,375,588 A | 12/1994 | Yoon |
| 5,378,588 A | 1/1995 | Tsuchiya |
| 5,380,291 A | 1/1995 | Kaali |
| 5,382,297 A | 1/1995 | Valentine et al. |
| 5,385,552 A | 1/1995 | Haber et al. |
| 5,385,553 A | 1/1995 | Hart et al. |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,392,766 A | 2/1995 | Masterson et al. |
| 5,394,863 A | 3/1995 | Sanford et al. |
| 5,395,367 A | 3/1995 | Wilk |
| 5,400,767 A | 3/1995 | Murdoch |
| 5,407,427 A | 4/1995 | Zhu et al. |
| 5,407,433 A | 4/1995 | Loomas |
| 5,407,434 A | 4/1995 | Gross |
| 5,419,312 A | 5/1995 | Arenberg et al. |
| 5,429,609 A | 7/1995 | Yoon |
| 5,431,151 A | 7/1995 | Riek et al. |
| 5,437,683 A | 8/1995 | Neumann et al. |
| 5,441,486 A | 8/1995 | Yoon |
| 5,445,615 A | 8/1995 | Yoon |
| 5,451,222 A | 9/1995 | De Maagd et al. |
| 5,460,170 A | 10/1995 | Hammerslag |
| 5,460,616 A | 10/1995 | Weinstein et al. |
| 5,463,010 A | 10/1995 | Hu et al. |
| 5,464,409 A | 11/1995 | Mohajer |
| 5,480,410 A | 1/1996 | Cuschieri et al. |
| 5,484,420 A | 1/1996 | Russo |
| 5,484,425 A | 1/1996 | Fischell et al. |
| 5,490,843 A | 2/1996 | Hildwein et al. |
| 5,505,707 A | 4/1996 | Manzie et al. |
| 5,507,758 A | 4/1996 | Thomason et al. |
| 5,511,564 A | 4/1996 | Wilk |
| 5,514,084 A | 5/1996 | Fisher |
| 5,514,109 A | 5/1996 | Mollenauer et al. |
| 5,514,133 A | 5/1996 | Golub et al. |
| 5,514,153 A | 5/1996 | Bonutti |
| 5,518,502 A | 5/1996 | Kaplan et al. |
| 5,520,610 A | 5/1996 | Giglio et al. |
| 5,520,698 A | 5/1996 | Koh |
| 5,522,791 A | 6/1996 | Leyva |
| 5,524,501 A | 6/1996 | Patterson et al. |
| 5,524,644 A | 6/1996 | Crook |
| 5,538,509 A | 7/1996 | Dunlap et al. |
| 5,540,648 A | 7/1996 | Yoon |
| 5,542,931 A | 8/1996 | Gravener et al. |
| 5,545,150 A | 8/1996 | Danks et al. |
| 5,545,179 A | 8/1996 | Williamson, IV |
| 5,549,565 A | 8/1996 | Ryan et al. |
| 5,550,363 A | 8/1996 | Obata |
| 5,551,947 A | 9/1996 | Kaali |
| 5,556,385 A | 9/1996 | Andersen |
| 5,556,387 A | 9/1996 | Mollenauer et al. |
| 5,569,159 A | 10/1996 | Anderson et al. |
| 5,569,205 A | 10/1996 | Hart et al. |
| 5,569,291 A | 10/1996 | Privitera et al. |
| 5,569,292 A | 10/1996 | Scwemberger et al. |
| 5,577,993 A | 11/1996 | Zhu et al. |
| 5,591,192 A | 1/1997 | Privitera et al. |
| 5,601,581 A | 2/1997 | Fogarty et al. |
| 5,603,702 A | 2/1997 | Smith et al. |
| 5,609,562 A | 3/1997 | Kaali |
| 5,624,399 A | 4/1997 | Ackerman |
| 5,628,732 A | 5/1997 | Antoon, Jr. et al. |
| 5,630,795 A | 5/1997 | Kuramoto et al. |
| 5,634,908 A | 6/1997 | Loomas |
| 5,634,911 A | 6/1997 | Hermann et al. |

(56) References Cited

U.S. PATENT DOCUMENTS

| | | |
|---|---|---|
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,662,615 A | 9/1997 | Blake, III |
| 5,666,222 A | 9/1997 | Ning |
| 5,672,168 A | 9/1997 | de la Torre et al. |
| 5,674,181 A | 10/1997 | Iida |
| 5,683,378 A | 11/1997 | Christy |
| 5,685,820 A | 11/1997 | Riek et al. |
| 5,685,823 A | 11/1997 | Ito et al. |
| 5,685,857 A | 11/1997 | Negus et al. |
| 5,685,862 A | 11/1997 | Mahurkar |
| 5,697,946 A | 12/1997 | Hopper et al. |
| 5,709,671 A | 1/1998 | Stephens et al. |
| 5,709,675 A | 1/1998 | Williams |
| 5,713,858 A | 2/1998 | Heruth et al. |
| 5,713,869 A | 2/1998 | Morejon |
| 5,720,730 A | 2/1998 | Blake, III |
| 5,720,759 A | 2/1998 | Green et al. |
| 5,720,761 A | 2/1998 | Kaali |
| 5,722,958 A | 3/1998 | Gravener et al. |
| 5,722,962 A | 3/1998 | Garcia |
| 5,725,477 A | 3/1998 | Yasui et al. |
| 5,728,103 A | 3/1998 | Picha et al. |
| 5,730,748 A | 3/1998 | Fogarty et al. |
| 5,735,791 A | 4/1998 | Alexander, Jr. et al. |
| 5,735,792 A | 4/1998 | Vanden Hoek et al. |
| 5,738,664 A | 4/1998 | Erskine et al. |
| 5,741,298 A | 4/1998 | MacLeod |
| 5,743,884 A | 4/1998 | Hasson et al. |
| 5,752,970 A | 5/1998 | Yoon |
| 5,755,782 A | 5/1998 | Love et al. |
| 5,776,112 A | 7/1998 | Stephens et al. |
| 5,779,697 A | 7/1998 | Glowa et al. |
| 5,782,817 A | 7/1998 | Franzel et al. |
| 5,788,676 A | 8/1998 | Yoon |
| 5,792,112 A | 8/1998 | Hart et al. |
| 5,792,113 A | 8/1998 | Kramer et al. |
| 5,795,290 A | 8/1998 | Bridges |
| 5,800,451 A | 9/1998 | Buess et al. |
| 5,803,921 A | 9/1998 | Bonadio |
| 5,810,712 A | 9/1998 | Dunn |
| 5,813,409 A | 9/1998 | Leahy et al. |
| 5,817,061 A | 10/1998 | Goodwin et al. |
| 5,820,600 A | 10/1998 | Carlson et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,843,031 A | 12/1998 | Hermann |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,471 A | 2/1999 | Ryan et al. |
| 5,871,474 A | 2/1999 | Hermann et al. |
| 5,876,413 A | 3/1999 | Fogarty et al. |
| 5,893,875 A | 4/1999 | O'Connor et al. |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,900,971 A | 5/1999 | Ning |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,931,833 A | 8/1999 | Silverstein |
| 5,941,898 A | 8/1999 | Moenning et al. |
| 5,944,654 A | 8/1999 | Crawford |
| 5,951,588 A | 9/1999 | Moenning |
| 5,957,913 A | 9/1999 | de la Torre et al. |
| 5,960,145 A | 9/1999 | Sanchez |
| 5,964,781 A | 10/1999 | Mollenauer et al. |
| 5,976,174 A | 11/1999 | Ruiz |
| 5,989,233 A | 11/1999 | Yoon |
| 5,997,515 A | 12/1999 | de la Torre et al. |
| 6,007,481 A | 12/1999 | Riek et al. |
| 6,017,355 A | 1/2000 | Hessel et al. |
| 6,017,356 A | 1/2000 | Frederick et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,079,692 A | 6/2000 | Powell |
| 6,086,603 A | 7/2000 | Termin et al. |
| 6,093,176 A | 7/2000 | Dennis |
| 6,099,505 A | 8/2000 | Ryan et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,213,957 B1 | 4/2001 | Milliman et al. |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,333,051 B1 | 12/2001 | Kabanov et al. |
| 6,354,992 B1 | 3/2002 | Kato |
| 6,355,014 B1 | 3/2002 | Zadno-Azizi et al. |
| 6,355,028 B2 | 3/2002 | Castaneda et al. |
| 6,371,968 B1 | 4/2002 | Kogasaka et al. |
| 6,382,211 B1 | 5/2002 | Crook |
| 6,387,044 B1 | 5/2002 | Tachibana et al. |
| 6,416,506 B1 | 7/2002 | Tilton, Jr. et al. |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,458,076 B1 | 10/2002 | Pruitt |
| 6,464,686 B1 | 10/2002 | O'Hara et al. |
| 6,468,292 B1 | 10/2002 | Mollenauer et al. |
| 6,478,806 B2 | 11/2002 | McFarlane |
| 6,482,181 B1 | 11/2002 | Racenet et al. |
| 6,485,410 B1 | 11/2002 | Loy |
| 6,485,467 B1 | 11/2002 | Crook et al. |
| 6,487,806 B2 | 12/2002 | Murello et al. |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,749 B1 | 3/2003 | Roby et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,551,283 B1 | 4/2003 | Guo et al. |
| 6,554,793 B1 | 4/2003 | Pauker et al. |
| 6,558,371 B2 | 5/2003 | Dorn |
| 6,562,022 B2 | 5/2003 | Hoste et al. |

(56) References Cited

U.S. PATENT DOCUMENTS

| | | |
|---|---|---|
| 6,569,120 B1 | 5/2003 | Green et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,602,240 B2 | 8/2003 | Hermann et al. |
| 6,610,031 B1 | 8/2003 | Chin |
| 6,613,038 B2 | 9/2003 | Bonutti et al. |
| 6,613,952 B2 | 9/2003 | Rambo |
| 6,623,426 B2 | 9/2003 | Bonadio et al. |
| 6,632,929 B1 | 10/2003 | Wilchek et al. |
| 6,638,508 B2 | 10/2003 | Schechter et al. |
| 6,648,922 B2 | 11/2003 | Ung-Chhun et al. |
| 6,663,598 B1 | 12/2003 | Carrillo, Jr. et al. |
| 6,669,674 B1 | 12/2003 | Macoviak et al. |
| 6,676,639 B1 | 1/2004 | Ternstrom |
| 6,682,165 B2 | 1/2004 | Yearout |
| 6,684,405 B2 | 2/2004 | Lezdey |
| 6,702,787 B2 | 3/2004 | Racenet et al. |
| 6,706,050 B1 | 3/2004 | Giannadakis |
| 6,712,791 B2 | 3/2004 | Lui et al. |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,736,797 B1 | 5/2004 | Larsen et al. |
| 6,740,064 B1 | 5/2004 | Sorrentino et al. |
| 6,755,782 B2 | 6/2004 | Ogawa |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,835,201 B2 | 12/2004 | O'Heeron et al. |
| 6,837,893 B2 | 1/2005 | Miller |
| 6,840,909 B2 | 1/2005 | Gatto |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,855,128 B2 | 2/2005 | Swenson |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,923,759 B2 | 8/2005 | Kasahara et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,960,164 B2 | 11/2005 | O'Heeron |
| 6,966,906 B2 | 11/2005 | Brown |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,044,974 B2 | 5/2006 | Garber et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,062 B2 | 6/2007 | Brustad |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,300,445 B2 | 11/2007 | Adams |
| 7,300,448 B2 | 11/2007 | Criscuolo et al. |
| 7,316,683 B2 | 1/2008 | Kasahara et al. |
| 7,316,699 B2 | 1/2008 | McFarlane |
| 7,320,694 B2 | 1/2008 | O'Heeron |
| 7,331,940 B2 | 2/2008 | Sommerich |
| 7,339,341 B2 | 3/2008 | Oleynikov et al. |
| 7,344,547 B2 | 3/2008 | Piskun |
| 7,370,694 B2 | 5/2008 | Shimizu et al. |
| 7,377,898 B2 | 5/2008 | Ewers et al. |
| 7,390,317 B2 | 6/2008 | Taylor et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,485,092 B1 | 2/2009 | Stewart et al. |
| 7,493,703 B2 | 2/2009 | Kim et al. |
| 7,494,481 B2 | 2/2009 | Moberg et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,530,984 B2 | 5/2009 | Sonnenschein et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,582,071 B2 | 9/2009 | Wenchell |
| 7,596,828 B2 | 10/2009 | Evdokimo |
| 7,608,082 B2 | 10/2009 | Cuevas et al. |
| 7,625,361 B2 | 12/2009 | Suzuki et al. |
| 7,632,250 B2 | 12/2009 | Smith et al. |
| 7,645,232 B2 | 1/2010 | Shluzas |
| 7,650,887 B2 | 1/2010 | Nguyen et al. |
| 7,678,046 B2 | 3/2010 | White et al. |
| 7,686,823 B2 | 3/2010 | Pingleton et al. |
| 7,691,089 B2 | 4/2010 | Gresham |
| 7,699,191 B2 | 4/2010 | Sheets, Jr. et al. |
| 7,704,207 B2 | 4/2010 | Albrecht et al. |
| 7,708,713 B2 | 5/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,744,569 B2 | 6/2010 | Smith |
| 7,753,901 B2 | 7/2010 | Piskun et al. |
| 7,758,500 B2 | 7/2010 | Boyd et al. |
| 7,758,603 B2 | 7/2010 | Taylor et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,794,644 B2 | 9/2010 | Taylor et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,824,419 B2 | 11/2010 | Boraiah |
| 7,837,612 B2 | 11/2010 | Gill et al. |

(56) References Cited

U.S. PATENT DOCUMENTS

| | | |
|---|---|---|
| 7,846,107 B2 | 12/2010 | Hoffman et al. |
| 7,846,123 B2 | 12/2010 | Vassiliades et al. |
| 7,850,600 B1 | 12/2010 | Piskun |
| 7,850,655 B2 | 12/2010 | Pasqualucci |
| 7,850,667 B2 | 12/2010 | Gresham |
| 7,858,079 B2 | 12/2010 | Hadba et al. |
| 7,867,164 B2 | 1/2011 | Butler et al. |
| 7,896,847 B2 | 3/2011 | Wenchell |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,918,827 B2 | 4/2011 | Smith |
| 7,922,701 B2 | 4/2011 | Buchman |
| 7,931,624 B2 | 4/2011 | Smith et al. |
| 7,947,058 B2 | 5/2011 | Kahle et al. |
| 7,951,076 B2 | 5/2011 | Hart et al. |
| 7,951,118 B2 | 5/2011 | Smith et al. |
| 7,955,257 B2 | 6/2011 | Frasier et al. |
| 7,955,313 B2 | 6/2011 | Boismier |
| 7,959,561 B2 | 6/2011 | Akui et al. |
| 7,985,232 B2 | 7/2011 | Potter et al. |
| 7,998,068 B2 | 8/2011 | Bonadio et al. |
| 8,002,750 B2 | 8/2011 | Smith |
| 8,002,786 B2 | 8/2011 | Beckman et al. |
| 8,012,128 B2 | 9/2011 | Franer et al. |
| 8,021,296 B2 | 9/2011 | Bonadio et al. |
| 8,025,670 B2 | 9/2011 | Sharp et al. |
| 8,029,475 B2 | 10/2011 | Franer et al. |
| 8,038,652 B2 | 10/2011 | Morrison et al. |
| 8,052,653 B2 | 11/2011 | Gratwohl et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,092,431 B2 | 1/2012 | Lunn et al. |
| 8,105,234 B2 | 1/2012 | Ewers et al. |
| 8,109,873 B2 | 2/2012 | Albrecht et al. |
| 8,109,943 B2 | 2/2012 | Boraiah et al. |
| 8,118,735 B2 | 2/2012 | Voegele |
| 8,128,590 B2 | 3/2012 | Albrecht et al. |
| 8,137,318 B2 | 3/2012 | Schweitzer et al. |
| 8,137,322 B2 | 3/2012 | Soltz et al. |
| 8,147,453 B2 | 4/2012 | Albrecht et al. |
| 8,152,828 B2 | 4/2012 | Taylor et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,206,411 B2 | 6/2012 | Thompson et al. |
| 8,241,209 B2 | 8/2012 | Shelton, IV et al. |
| 8,262,568 B2 | 9/2012 | Albrecht et al. |
| 8,267,952 B2 | 9/2012 | Kahle et al. |
| 8,287,503 B2 | 10/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,398,666 B2 | 3/2013 | McFarlane |
| 8,403,883 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 8,597,180 B2 | 12/2013 | Copeland et al. |
| 8,961,406 B2 | 2/2015 | Ortiz et al. |
| 9,022,986 B2 | 5/2015 | Gresham |
| 9,572,580 B2 | 2/2017 | Sargeant et al. |
| 10,022,149 B2 | 7/2018 | Holsten et al. |
| 10,299,778 B2 | 5/2019 | Richard et al. |
| 10,568,660 B2 | 2/2020 | Zhou |
| 2001/0037053 A1 | 11/2001 | Bonadio et al. |
| 2001/0041871 A1 | 11/2001 | Brimhall |
| 2001/0044570 A1 | 11/2001 | Ouchi et al. |
| 2001/0049499 A1 | 12/2001 | Lui et al. |
| 2001/0049508 A1 | 12/2001 | Fangrow, Jr. et al. |
| 2002/0013552 A1 | 1/2002 | Dennis |
| 2002/0016556 A1 | 2/2002 | Williams |
| 2002/0022266 A1 | 2/2002 | Wagner et al. |
| 2002/0022762 A1 | 2/2002 | Beane et al. |
| 2002/0035311 A1 | 3/2002 | Ouchi |
| 2002/0055714 A1 | 5/2002 | Rothschild |
| 2002/0065450 A1 | 5/2002 | Ogawa |
| 2002/0091410 A1 | 7/2002 | Ben-David et al. |
| 2002/0128234 A1 | 9/2002 | Hubbell et al. |
| 2002/0173748 A1 | 11/2002 | McConnell et al. |
| 2002/0183775 A1 | 12/2002 | Tsonton et al. |
| 2003/0014076 A1 | 1/2003 | Mollenauer et al. |
| 2003/0022216 A1 | 1/2003 | Mao et al. |
| 2003/0032858 A1 | 2/2003 | Ginn et al. |
| 2003/0040711 A1 | 2/2003 | Racenet et al. |
| 2003/0050604 A1 | 3/2003 | Lui et al. |
| 2003/0073955 A1 | 4/2003 | Otawara |
| 2003/0093104 A1 | 5/2003 | Bonner et al. |
| 2003/0109853 A1 | 6/2003 | Harding et al. |
| 2003/0139756 A1 | 7/2003 | Brustad |
| 2003/0153001 A1 | 8/2003 | Soane et al. |
| 2003/0158572 A1 | 8/2003 | McFarlane |
| 2003/0181423 A1 | 9/2003 | Clapper et al. |
| 2003/0187376 A1 | 10/2003 | Rambo |
| 2003/0187424 A1 | 10/2003 | Chu et al. |
| 2003/0195472 A1 | 10/2003 | Green et al. |
| 2003/0208104 A1 | 11/2003 | Carrillo, Jr. et al. |
| 2003/0233115 A1 | 12/2003 | Eversull et al. |
| 2003/0236549 A1 | 12/2003 | Bonadio et al. |
| 2004/0015185 A1 | 1/2004 | Ewers et al. |
| 2004/0023413 A1 | 2/2004 | Opalsky |
| 2004/0054353 A1 | 3/2004 | Taylor |
| 2004/0059297 A1 | 3/2004 | Racenet et al. |
| 2004/0066008 A1 | 4/2004 | Smith |
| 2004/0068232 A1 | 4/2004 | Hart et al. |
| 2004/0073090 A1 | 4/2004 | Butler et al. |
| 2004/0092795 A1 | 5/2004 | Bonadio et al. |
| 2004/0093018 A1 | 5/2004 | Johnson |
| 2004/0102804 A1 | 5/2004 | Chin |
| 2004/0106942 A1 | 6/2004 | Taylor et al. |
| 2004/0111060 A1 | 6/2004 | Racenet et al. |
| 2004/0111061 A1 | 6/2004 | Curran |
| 2004/0138529 A1 | 7/2004 | Wiltshire et al. |
| 2004/0138702 A1 | 7/2004 | Peartree et al. |
| 2004/0186434 A1 | 9/2004 | Harding et al. |
| 2004/0193113 A1 | 9/2004 | Gillis et al. |
| 2004/0204682 A1 | 10/2004 | Smith |
| 2004/0204734 A1 | 10/2004 | Wagner et al. |
| 2004/0215209 A1 | 10/2004 | Almond et al. |
| 2004/0254426 A1 | 12/2004 | Wenchell |
| 2004/0267096 A1 | 12/2004 | Caldwell et al. |
| 2004/0267204 A1 | 12/2004 | Brustowicz |
| 2005/0010238 A1 | 1/2005 | Potter et al. |
| 2005/0020884 A1 | 1/2005 | Hart et al. |
| 2005/0033237 A1 | 2/2005 | Fentress et al. |
| 2005/0033342 A1 | 2/2005 | Hart et al. |
| 2005/0059934 A1 | 3/2005 | Wenchell et al. |
| 2005/0065543 A1 | 3/2005 | Kahle et al. |
| 2005/0070850 A1 | 3/2005 | Albrecht |
| 2005/0070851 A1 | 3/2005 | Thompson et al. |
| 2005/0070935 A1 | 3/2005 | Ortiz |
| 2005/0070946 A1 | 3/2005 | Franer et al. |
| 2005/0070947 A1 | 3/2005 | Franer et al. |
| 2005/0096605 A1* | 5/2005 | Green .................. A61M 39/06 604/246 |
| 2005/0096695 A1 | 5/2005 | Olich |
| 2005/0107816 A1 | 5/2005 | Pingleton et al. |
| 2005/0119525 A1 | 6/2005 | Takemoto |
| 2005/0119613 A1 | 6/2005 | Moenning et al. |
| 2005/0137459 A1 | 6/2005 | Chin et al. |
| 2005/0148823 A1 | 7/2005 | Vaugh et al. |
| 2005/0149096 A1 | 7/2005 | Hilal et al. |
| 2005/0153090 A1 | 7/2005 | Marchitto et al. |
| 2005/0165433 A1 | 7/2005 | Haberland et al. |
| 2005/0182443 A1 | 8/2005 | Jonn et al. |
| 2005/0192483 A1 | 9/2005 | Bonadio et al. |
| 2005/0192594 A1 | 9/2005 | Skakoon et al. |
| 2005/0203346 A1 | 9/2005 | Bonadio et al. |
| 2005/0209608 A1 | 9/2005 | O'Heeron |
| 2005/0212221 A1 | 9/2005 | Smith et al. |

(56) References Cited

U.S. PATENT DOCUMENTS

| | | |
|---|---|---|
| 2005/0222582 A1 | 10/2005 | Wenchell |
| 2005/0244453 A1 | 11/2005 | Stucke et al. |
| 2005/0245876 A1 | 11/2005 | Khosravi et al. |
| 2005/0251092 A1 | 11/2005 | Howell et al. |
| 2005/0251190 A1 | 11/2005 | McFarlane |
| 2005/0267419 A1 | 12/2005 | Smith |
| 2005/0272975 A1 | 12/2005 | McWeeney et al. |
| 2005/0277946 A1 | 12/2005 | Greenhalgh |
| 2005/0281802 A1 | 12/2005 | Gong et al. |
| 2005/0288622 A1 | 12/2005 | Albrecht et al. |
| 2006/0020281 A1 | 1/2006 | Smith |
| 2006/0025815 A1 | 2/2006 | McGurk et al. |
| 2006/0041232 A1 | 2/2006 | Stearns et al. |
| 2006/0047284 A1 | 3/2006 | Gresham |
| 2006/0047293 A1 | 3/2006 | Haberland et al. |
| 2006/0071432 A1 | 4/2006 | Staudner |
| 2006/0079918 A1 | 4/2006 | Creston |
| 2006/0084842 A1 | 4/2006 | Hart et al. |
| 2006/0129165 A1 | 6/2006 | Edoga et al. |
| 2006/0149137 A1 | 7/2006 | Pingleton et al. |
| 2006/0149305 A1 | 7/2006 | Cuevas et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0211992 A1 | 9/2006 | Prosek |
| 2006/0212063 A1 | 9/2006 | Wilk |
| 2006/0217665 A1 | 9/2006 | Prosek |
| 2006/0224120 A1 | 10/2006 | Smith et al. |
| 2006/0224161 A1 | 10/2006 | Bhattacharyya |
| 2006/0224174 A1 | 10/2006 | Smith et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0264991 A1 | 11/2006 | Johnson et al. |
| 2006/0270911 A1 | 11/2006 | Voegele et al. |
| 2006/0276751 A1 | 12/2006 | Haberland et al. |
| 2006/0293559 A1 | 12/2006 | Grice et al. |
| 2007/0055107 A1 | 3/2007 | Wenchell |
| 2007/0073248 A1 | 3/2007 | Moenning |
| 2007/0075465 A1 | 4/2007 | Taylor et al. |
| 2007/0088241 A1 | 4/2007 | Brustad et al. |
| 2007/0088274 A1 | 4/2007 | Stubbs et al. |
| 2007/0088277 A1 | 4/2007 | McGinley et al. |
| 2007/0093695 A1 | 4/2007 | Bonadio et al. |
| 2007/0112361 A1 | 5/2007 | Schonholz et al. |
| 2007/0116854 A1 | 5/2007 | Taylor et al. |
| 2007/0118175 A1 | 5/2007 | Butler et al. |
| 2007/0129719 A1 | 6/2007 | Kendale et al. |
| 2007/0149850 A1 | 6/2007 | Spivey et al. |
| 2007/0151566 A1 | 7/2007 | Kahle et al. |
| 2007/0185453 A1 | 8/2007 | Michael et al. |
| 2007/0197972 A1 | 8/2007 | Racenet et al. |
| 2007/0203398 A1 | 8/2007 | Bonadio et al. |
| 2007/0208220 A1 | 9/2007 | Carter |
| 2007/0208221 A1 | 9/2007 | Kennedy et al. |
| 2007/0208312 A1 | 9/2007 | Norton et al. |
| 2007/0213667 A1 | 9/2007 | Prusmack |
| 2007/0225650 A1 | 9/2007 | Hart et al. |
| 2007/0233006 A1 | 10/2007 | Brustad |
| 2007/0239108 A1 | 10/2007 | Albrecht et al. |
| 2007/0255218 A1 | 11/2007 | Franer |
| 2007/0260121 A1 | 11/2007 | Bakos et al. |
| 2007/0270654 A1 | 11/2007 | Pignato et al. |
| 2007/0270882 A1 | 11/2007 | Hjelle et al. |
| 2007/0282253 A1 | 12/2007 | Sasaki |
| 2007/0282356 A1 | 12/2007 | Sonnenschein et al. |
| 2007/0286891 A1 | 12/2007 | Kettlewell et al. |
| 2007/0293719 A1 | 12/2007 | Scopton et al. |
| 2007/0299310 A1 | 12/2007 | Phillips |
| 2008/0009826 A1 | 1/2008 | Miller et al. |
| 2008/0011307 A1 | 1/2008 | Beckman et al. |
| 2008/0015618 A1 | 1/2008 | Sonnenschein et al. |
| 2008/0021360 A1 | 1/2008 | Fihe et al. |
| 2008/0027476 A1 | 1/2008 | Piskun |
| 2008/0033363 A1 | 2/2008 | Haberland et al. |
| 2008/0048011 A1 | 2/2008 | Weller |
| 2008/0051739 A1 | 2/2008 | McFarlane |
| 2008/0058723 A1 | 3/2008 | Lipchitz et al. |
| 2008/0058852 A1 | 3/2008 | Ihde |
| 2008/0077169 A1 | 3/2008 | Taylor et al. |
| 2008/0081948 A1 | 4/2008 | Weisenburgh et al. |
| 2008/0086074 A1 | 4/2008 | Taylor et al. |
| 2008/0086160 A1 | 4/2008 | Mastri et al. |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0125716 A1 | 5/2008 | Cruz |
| 2008/0146884 A1 | 6/2008 | Beckman et al. |
| 2008/0161826 A1 | 7/2008 | Guiraudon |
| 2008/0161837 A1 | 7/2008 | Toso et al. |
| 2008/0177265 A1 | 7/2008 | Lechot |
| 2008/0188715 A1 | 8/2008 | Fujimoto |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0208222 A1 | 8/2008 | Beckman et al. |
| 2008/0220029 A1 | 9/2008 | Ng et al. |
| 2008/0221628 A1 | 9/2008 | Milbocker et al. |
| 2008/0249475 A1 | 10/2008 | Albrecht et al. |
| 2008/0255519 A1 | 10/2008 | Piskun et al. |
| 2008/0300617 A1 | 12/2008 | Smith |
| 2008/0302487 A1 | 12/2008 | Goodman et al. |
| 2008/0319261 A1 | 12/2008 | Lucini et al. |
| 2008/0319266 A1 | 12/2008 | Poll et al. |
| 2009/0005799 A1 | 1/2009 | Franer et al. |
| 2009/0012477 A1 | 1/2009 | Norton et al. |
| 2009/0023986 A1 | 1/2009 | Stewart et al. |
| 2009/0030443 A1 | 1/2009 | Buser et al. |
| 2009/0036738 A1 | 2/2009 | Cuschieri et al. |
| 2009/0036745 A1 | 2/2009 | Bonadio et al. |
| 2009/0048683 A1 | 2/2009 | Morris et al. |
| 2009/0049627 A1 | 2/2009 | Kritzler |
| 2009/0076465 A1 | 3/2009 | Berry et al. |
| 2009/0093752 A1 | 4/2009 | Richard et al. |
| 2009/0093835 A1 | 4/2009 | Heinrich et al. |
| 2009/0093850 A1 | 4/2009 | Richard |
| 2009/0105543 A1 | 4/2009 | Miller et al. |
| 2009/0105635 A1 | 4/2009 | Bettuchi et al. |
| 2009/0112065 A1 | 4/2009 | Harrel |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221966 A1 | 9/2009 | Richard |
| 2009/0221968 A1 | 9/2009 | Morrison et al. |
| 2009/0227843 A1 | 9/2009 | Smith et al. |
| 2009/0234193 A1 | 9/2009 | Weisenburgh, III et al. |
| 2009/0234293 A1 | 9/2009 | Albrecht et al. |
| 2009/0234376 A1 | 9/2009 | Soltz et al. |
| 2009/0240111 A1 | 9/2009 | Kessler et al. |
| 2009/0264703 A1 | 10/2009 | Pribanic |
| 2009/0270681 A1 | 10/2009 | Moreno et al. |
| 2009/0270685 A1 | 10/2009 | Moreno et al. |
| 2009/0270686 A1 | 10/2009 | Duke et al. |
| 2009/0270813 A1 | 10/2009 | Moreno et al. |
| 2009/0270817 A1 | 10/2009 | Moreno et al. |
| 2009/0270818 A1 | 10/2009 | Duke |
| 2009/0287052 A1 | 11/2009 | Amos et al. |
| 2009/0326330 A1 | 12/2009 | Bonadio et al. |
| 2009/0326332 A1 | 12/2009 | Carter |
| 2010/0004599 A1 | 1/2010 | Zhou et al. |
| 2010/0016664 A1 | 1/2010 | Viola |
| 2010/0016800 A1 | 1/2010 | Rockrohr |
| 2010/0022958 A1 | 1/2010 | Moreno, Jr. et al. |
| 2010/0030031 A1 | 2/2010 | Goldfarb et al. |
| 2010/0030155 A1 | 2/2010 | Gyrn et al. |

(56) References Cited

U.S. PATENT DOCUMENTS

| | | |
|---|---|---|
| 2010/0049138 A1 | 2/2010 | Smith et al. |
| 2010/0063450 A1 | 3/2010 | Smith et al. |
| 2010/0063452 A1 | 3/2010 | Edelman et al. |
| 2010/0094393 A1 | 4/2010 | Cordeiro et al. |
| 2010/0100043 A1 | 4/2010 | Racenet |
| 2010/0113886 A1 | 5/2010 | Piskun et al. |
| 2010/0174144 A1 | 7/2010 | Hsu et al. |
| 2010/0222801 A1 | 9/2010 | Pingleton et al. |
| 2010/0228090 A1 | 9/2010 | Weisenburgh, II |
| 2010/0228094 A1* | 9/2010 | Ortiz ............... A61B 17/0293 600/205 |
| 2010/0228096 A1 | 9/2010 | Weisenburgh, II et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0256453 A1 | 10/2010 | Hammond et al. |
| 2010/0261975 A1 | 10/2010 | Huey et al. |
| 2010/0262080 A1 | 10/2010 | Shelton, IV et al. |
| 2010/0280326 A1 | 11/2010 | Hess et al. |
| 2010/0285088 A1 | 11/2010 | Sargeant et al. |
| 2010/0286484 A1 | 11/2010 | Stellon et al. |
| 2010/0286506 A1 | 11/2010 | Ransden et al. |
| 2010/0286706 A1 | 11/2010 | Judson |
| 2010/0298646 A1 | 11/2010 | Stellon et al. |
| 2010/0312063 A1 | 12/2010 | Hess et al. |
| 2010/0318112 A1 | 12/2010 | Smith |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0087159 A1 | 4/2011 | Parihar et al. |
| 2011/0087168 A1 | 4/2011 | Parihar et al. |
| 2011/0087169 A1 | 4/2011 | Parihar et al. |
| 2011/0118553 A1 | 5/2011 | Stopek |
| 2011/0118833 A1 | 5/2011 | Reichenbach et al. |
| 2011/0124968 A1 | 5/2011 | Kleyman |
| 2011/0124969 A1 | 5/2011 | Stopek |
| 2011/0124970 A1 | 5/2011 | Kleyman |
| 2011/0124972 A1 | 5/2011 | Wenchell |
| 2011/0125186 A1 | 5/2011 | Fowler et al. |
| 2011/0152776 A1 | 6/2011 | Hartoumbekis et al. |
| 2011/0166423 A1 | 7/2011 | Farascioni et al. |
| 2011/0190592 A1 | 8/2011 | Kahle et al. |
| 2011/0196207 A1 | 8/2011 | Smith et al. |
| 2011/0201891 A1 | 8/2011 | Smith et al. |
| 2011/0230716 A1 | 9/2011 | Fujimoto |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251559 A1 | 10/2011 | Tal et al. |
| 2011/0251633 A1 | 10/2011 | Smith |
| 2011/0276002 A1 | 11/2011 | Bierman |
| 2011/0313242 A1 | 12/2011 | Surti |
| 2011/0313250 A1 | 12/2011 | Kleyman |
| 2012/0010569 A1 | 1/2012 | Parihar |
| 2012/0041371 A1 | 2/2012 | Tal et al. |
| 2012/0059640 A1 | 3/2012 | Roy et al. |
| 2012/0065590 A1 | 3/2012 | Bierman et al. |
| 2012/0109064 A1 | 5/2012 | Fischvogt et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0265022 A1 | 10/2012 | Menn |
| 2012/0283520 A1 | 11/2012 | Kleyman |
| 2012/0316596 A1 | 12/2012 | Taylor et al. |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2014/0249371 A1 | 9/2014 | Fischvogt |
| 2014/0257356 A1 | 9/2014 | Pacak et al. |
| 2015/0025477 A1 | 1/2015 | Evans |
| 2015/0065808 A1 | 3/2015 | Van Wyk et al. |
| 2015/0216560 A1* | 8/2015 | Holsten ............... A61B 17/0218 600/204 |
| 2018/0021063 A1* | 1/2018 | Main ..................... A61B 17/34 604/167.01 |
| 2018/0085145 A1* | 3/2018 | Okoniewski ....... A61B 17/0218 |
| 2019/0059938 A1* | 2/2019 | Holsten ............... A61B 17/3462 |
| 2019/0059944 A1* | 2/2019 | Holsten ............... A61B 17/3474 |

FOREIGN PATENT DOCUMENTS

| | | |
|---|---|---|
| CA | 2640388 C | 12/2015 |
| CN | 1907513 A | 2/2007 |
| CN | 202313634 U | 7/2012 |
| DE | 3217118 C1 | 8/1983 |
| DE | 3737121 A1 | 5/1989 |
| DE | 202008009527 U1 | 10/2008 |
| DE | 2008059633 | 6/2010 |
| EP | 0051718 A1 | 5/1982 |
| EP | 0113520 A2 | 7/1984 |
| EP | 0169787 A1 | 1/1986 |
| EP | 0226026 A2 | 6/1987 |
| EP | 0312219 A2 | 4/1989 |
| EP | 0538060 A1 | 4/1993 |
| EP | 0577400 A1 | 1/1994 |
| EP | 0630660 A1 | 12/1994 |
| EP | 0664992 A1 | 8/1995 |
| EP | 0807416 A2 | 11/1997 |
| EP | 0950376 A1 | 10/1999 |
| EP | 1188415 A2 | 3/2002 |
| EP | 1210904 A2 | 6/2002 |
| EP | 1312318 A1 | 5/2003 |
| EP | 1323373 A2 | 7/2003 |
| EP | 1629787 A2 | 3/2006 |
| EP | 1698291 A1 | 9/2006 |
| EP | 1774918 A1 | 4/2007 |
| EP | 1911409 A1 | 4/2008 |
| EP | 1932485 A1 | 6/2008 |
| EP | 1994896 A1 | 11/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2111782 A2 | 10/2009 |
| EP | 2138117 A1 | 12/2009 |

(56) References Cited

FOREIGN PATENT DOCUMENTS

| | | |
|---|---|---|
| EP | 2138118 A2 | 12/2009 |
| EP | 2145593 A1 | 1/2010 |
| EP | 2181657 A2 | 5/2010 |
| EP | 2226025 A1 | 9/2010 |
| EP | 2229897 A1 | 9/2010 |
| EP | 2229900 A1 | 9/2010 |
| EP | 2233090 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| EP | 2359782 A1 | 8/2011 |
| EP | 2361567 A1 | 8/2011 |
| EP | 3242615 A1 | 11/2017 |
| GB | 1482857 A | 8/1977 |
| GB | 2469083 | 4/2009 |
| JP | 58163867 | 9/1983 |
| JP | 06061518 | 4/1994 |
| JP | 07241298 | 9/1995 |
| JP | H08266548 A | 10/1996 |
| JP | 2004532660 A | 10/2004 |
| JP | 2005040184 A | 2/2005 |
| JP | 2005503230 A | 2/2005 |
| JP | 2005052229 A | 3/2005 |
| JP | 2006187603 A | 7/2006 |
| JP | 2006289083 A | 10/2006 |
| JP | 2007105314 A | 4/2007 |
| JP | 2007130167 A | 5/2007 |
| JP | 2007516737 A | 6/2007 |
| JP | 2008504886 A | 2/2008 |
| JP | 2008132282 A | 6/2008 |
| JP | 2008279202 A | 11/2008 |
| JP | 2008289889 A | 12/2008 |
| JP | 2008296027 A | 12/2008 |
| JP | 2009534124 A | 9/2009 |
| JP | 2010022758 A | 2/2010 |
| JP | 2011515128 A | 5/2011 |
| JP | 2011125709 A | 6/2011 |
| JP | 5103854 B2 | 12/2012 |
| WO | 8401512 | 4/1984 |
| WO | 9304717 A1 | 3/1993 |
| WO | 9314801 | 8/1993 |
| WO | 9404067 | 3/1994 |
| WO | 9417844 A1 | 8/1994 |
| WO | 9423759 A1 | 10/1994 |
| WO | 9513313 A1 | 5/1995 |
| WO | 9610963 | 4/1996 |
| WO | 9636283 | 11/1996 |
| WO | 9733520 | 9/1997 |
| WO | 9742889 | 11/1997 |
| WO | 9742991 A1 | 11/1997 |
| WO | 9824359 A1 | 6/1998 |
| WO | 9850093 A1 | 11/1998 |
| WO | 9853865 A1 | 12/1998 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0106829 A2 | 2/2001 |
| WO | 0108581 | 2/2001 |
| WO | 0149363 | 7/2001 |
| WO | 0185077 A1 | 11/2001 |
| WO | 0207611 | 1/2002 |
| WO | 02087682 A2 | 11/2002 |
| WO | 03000234 A1 | 1/2003 |
| WO | 03011154 A2 | 2/2003 |
| WO | 03034908 A2 | 5/2003 |
| WO | 03071926 | 9/2003 |
| WO | 03077726 | 9/2003 |
| WO | 03094760 A2 | 11/2003 |
| WO | 2004043275 | 5/2004 |
| WO | 2004043275 A1 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006063249 A2 | 6/2006 |
| WO | 2006100658 A2 | 9/2006 |
| WO | 2006110733 | 10/2006 |
| WO | 2006118650 A1 | 11/2006 |
| WO | 2007018458 | 2/2007 |
| WO | 2007095703 | 8/2007 |
| WO | 2007100882 A2 | 9/2007 |
| WO | 2007119232 A2 | 10/2007 |
| WO | 2007121425 A1 | 10/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2008153841 A2 | 12/2008 |
| WO | 2009018288 A1 | 2/2009 |
| WO | 2009036343 | 3/2009 |
| WO | 2010000047 | 1/2010 |
| WO | 2010141409 | 12/2010 |
| WO | 2010141673 | 12/2010 |
| WO | 2011011347 A2 | 1/2011 |
| WO | 2012131746 A1 | 10/2012 |
| WO | WO-2012131746 A1 * | 10/2012 ......... A61B 17/3462 |
| WO | 2014052532 A1 | 4/2014 |
| WO | 2016186905 A1 | 11/2016 |

* cited by examiner

VALVE ASSEMBLY AND RETAINER FOR SURGICAL ACCESS ASSEMBLY

FIELD

The present disclosure relates to assemblies including seals for minimally invasive surgery. More particularly, the present disclosure relates to valve assemblies and retainers for surgical access assemblies.

BACKGROUND

In order to facilitate minimally invasive surgery, a working space must be created at a surgical site. An insufflation fluid, typically $CO_2$, is introduced into the abdomen of the patient to create an inflated state called pneumoperitoneum. Surgical access assemblies are utilized to allow the introduction of surgical instrumentation and endoscopes (or other visualization tools). These surgical access assemblies maintain the pressure for the pneumoperitoneum, as they have one or more seals that adapt to the surgical instrumentation. Typically, a "zero-seal" in the surgical access assembly seals the surgical access assembly in the absence of a surgical instrument in the surgical access assembly, and an instrument seal seals around a surgical instrument that has been inserted through the surgical access assembly.

The breadth of surgical instrumentation on the market today requires a robust seal capable adjusting to multiple sizes and withstanding multiple insertions and withdrawals of surgical instrumentation. Some of the surgical instrumentation can include sharp edges that can tear or otherwise damage seals.

In addition to the instrument seal, a valve assembly also includes a guard and a centering mechanism. The guard helps minimize damage to the instrument seal during insertion and withdrawal of a surgical instrument through the valve assembly. A retainer is often used to maintain the position and alignment of the various components used in the valve assembly. The retainer may have multiple components that use posts and holes to join them together. As the posts need to extend through the various components in the valve assembly, the posts may also increase the assembly time of the valve assembly. A retainer without posts and corresponding holes would be beneficial.

SUMMARY

In embodiments, a surgical access assembly includes a cannula, a valve housing coupled to a proximal end of the cannula, and a valve assembly disposed in the valve housing. The valve assembly includes a centering mechanism, a ring, a retainer, a guard, and a seal. The centering mechanism includes a hoop having fingers extending radially outwards from an outer surface of the hoop. Each finger is flexibly connected to the outer surface and biased away from the outer surface. The ring has an outer diameter and a flange disposed at one end of the ring. The other end of the ring abuts one end of the hoop. The retainer has a first disc disposed in the ring and a second disc disposed in the hoop. The first disc is attachable to the second disc irrespective of the rotational orientation of the first disc relative to the second disc. The guard includes a frame and flaps flexibly coupled thereto. The guard is partially disposed in the first disc. The seal includes petals flexibly coupled to a support and the seal is partially disposed in the second disc.

The first disc may include a channel adapted to receive a portion of the frame and the second disc may include a groove adapted to receive a portion of the support. The second disc may include receptacles configured to receive protrusions of a plate.

One of the first or second discs may include a ridge circumscribing a central opening thereof and the other of the first or second discs may include a slot circumscribing a central opening thereof. The ridge may be adapted to fit within the slot for coupling the first and second discs together.

The first disc may be secured to the second disc. The first disc may be welded to the second disc.

In embodiments, a valve assembly for use in a surgical access assembly includes a guard, a seal, a centering mechanism, and a retainer. The guard includes a frame and flaps flexibly coupled thereto. The seal includes a support and petals flexibly coupled thereto. The centering mechanism includes a hoop and fingers. The fingers have first and second ends. The first ends of the fingers are flexibly coupled to an outer surface of the hoop and the second ends of the fingers are biased away from the outer surface. The retainer has first and second discs. The first disc has a ridge and the second disc has a slot configured to receive the ridge therein. One of the first or second discs is positionable in a passage defined by the hoop.

The valve assembly may be positionable in a housing of a surgical access assembly.

The first disc of the retainer may be securable to the second disc of the retainer irrespective of their relative angular orientations.

The valve assembly may include a plate disposed between the seal and the second disc.

The plate may include protrusions and the second disc may include receptacles for receiving the protrusions of the plate.

The guard and the seal may be located between the first and second discs of the retainer.

The valve assembly may include a ring abutting the hoop and the ring may be configured to receive the other of the first or second discs therein.

In embodiments, a surgical access assembly includes a valve housing, a cannula extending from the valve housing, and a valve assembly disposed in the valve housing. The valve assembly has a centering mechanism, a guard with a frame and flaps coupled to the frame, a seal with a support and petals coupled to the support, and a retainer including first and second discs. The centering mechanism has a hoop and fingers extending radially from the hoop. The guard is disposed on a first side of the centering mechanism and the seal is disposed on a second side of the centering mechanism. The guard is coupled to the first disc in a fixed orientation and the seal is coupled to the second disc in a fixed orientation. The first disc is attachable to the second disc irrespective of the rotational orientation of the first disc relative to the second disc.

The first disc may include a ridge and the second disc may include a slot for receiving the ridge therein. The first and second discs may be secured to one another. The first and second discs may be welded together.

The first disc may include a channel adapted to receive a portion of the frame and the second disc may include a groove adapted to receive a portion of the support.

BRIEF DESCRIPTION OF DRAWINGS

Embodiments of an instrument seal are disclosed herein with reference to the drawings, wherein.

DETAILED DESCRIPTION

Embodiments of the presently disclosed instrument seal for a surgical access assembly will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Surgical access assemblies are employed during minimally invasive surgery, e.g., laparoscopic surgery, and provide for the sealed access of surgical instruments into an insufflated body cavity, such as the abdominal cavity. The surgical access assemblies of the present disclosure include a valve housing mounted on a cannula tube, and include an obturator (not shown) inserted through the valve housing and cannula tube. The obturator can have a blunt distal end or a bladed or non-bladed penetrating distal end and can be used to incise the abdominal wall so that the surgical access assembly can be introduced into the abdomen. The handle of the obturator can engage or selectively lock into the valve housing of the surgical access assembly.

Surgical access assemblies with a trocar obturator are employed to tunnel through an anatomical structure, e.g., the abdominal wall, either by making a new passage through the structure or by passing through an existing opening through the anatomical structure. Once the surgical access assembly with the trocar has tunneled through the anatomical structure, the trocar obturator is removed, leaving the surgical access assembly in place. The valve housing of the surgical access assembly includes valves that prevent the escape of insufflation fluid from the body cavity, while also allowing surgical instruments to be inserted into the cavity and minimizing the escape of insufflation fluid.

In various embodiments, a bladeless optical trocar obturator may be provided that permits separation of tissue planes in a surgical procedure and visualization of body tissue fibers as they are being separated, thereby permitting a controlled traversal across a body wall. In other embodiments, the trocar obturator may be bladeless without being optical, e.g., without providing contemporaneous visualization thereof through the distal tip of the obturator. The bladeless obturator may be provided for the blunt dissection of the abdominal lining during a surgical procedure.

Various trocar obturators suitable for use with the surgical access assemblies of the present disclosure are known and include, for example, bladed, bladeless, blunt, optical, and non-optical. For a detailed description of the structure and function of exemplary trocar assemblies, including exemplar trocar obturators and exemplar cannulas, please refer to PCT Publication No. WO 2016/186905 ("the '905 publication"), the content of which is hereby incorporated by reference herein in its entirety.

Figure 1:
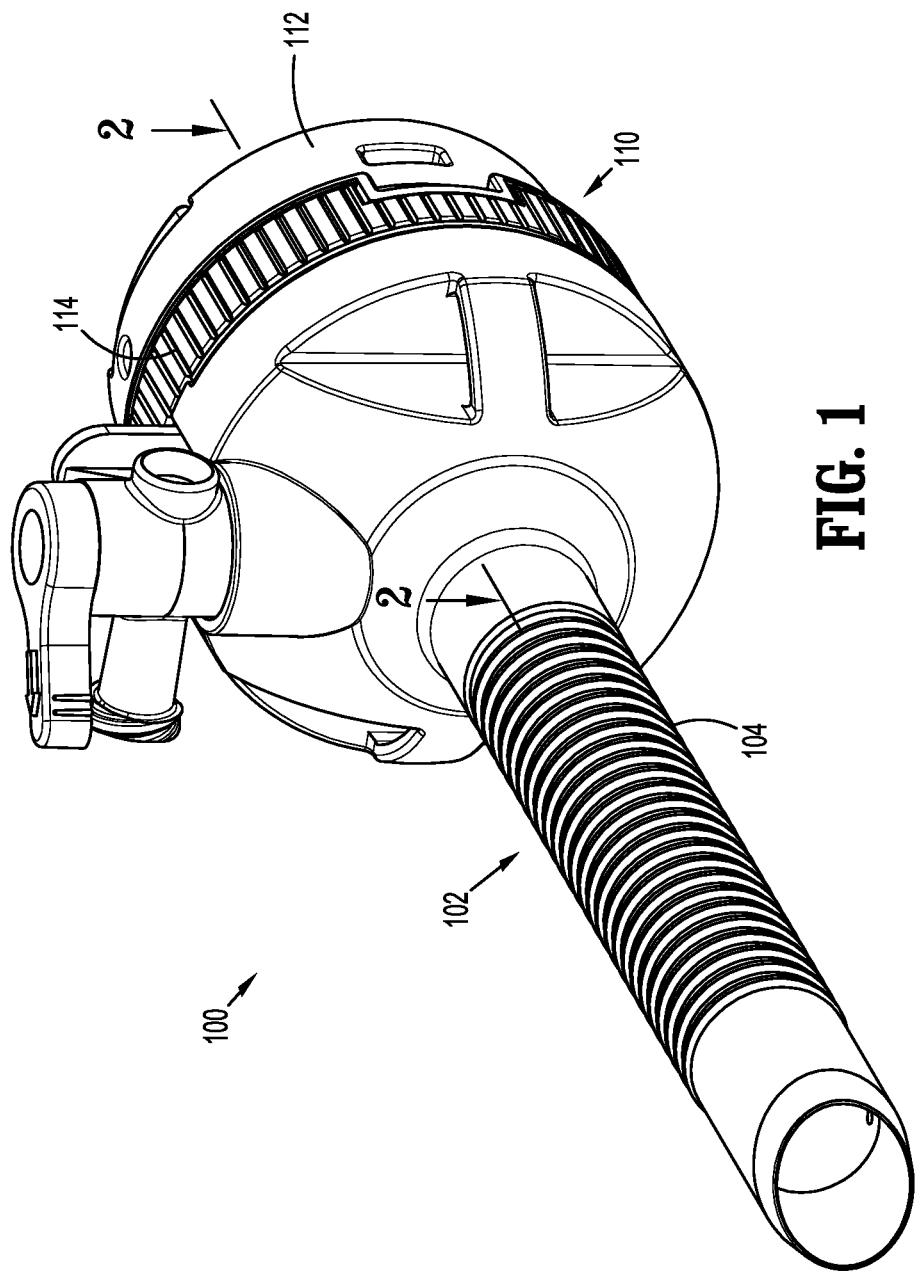
FIG. 1 is a perspective view of a surgical access assembly according to an embodiment of the present disclosure.

With initial reference now to FIG. 1, a surgical access assembly according to aspects of the present disclosure is shown generally as surgical access assembly 100. The surgical access assembly 100 includes a cannula 102 with a cannula tube 104 extending therefrom and a valve housing 110 secured to the cannula tube 104. For a detailed description of an exemplary surgical access assembly, please refer to the '905 publication.

Figure 2:
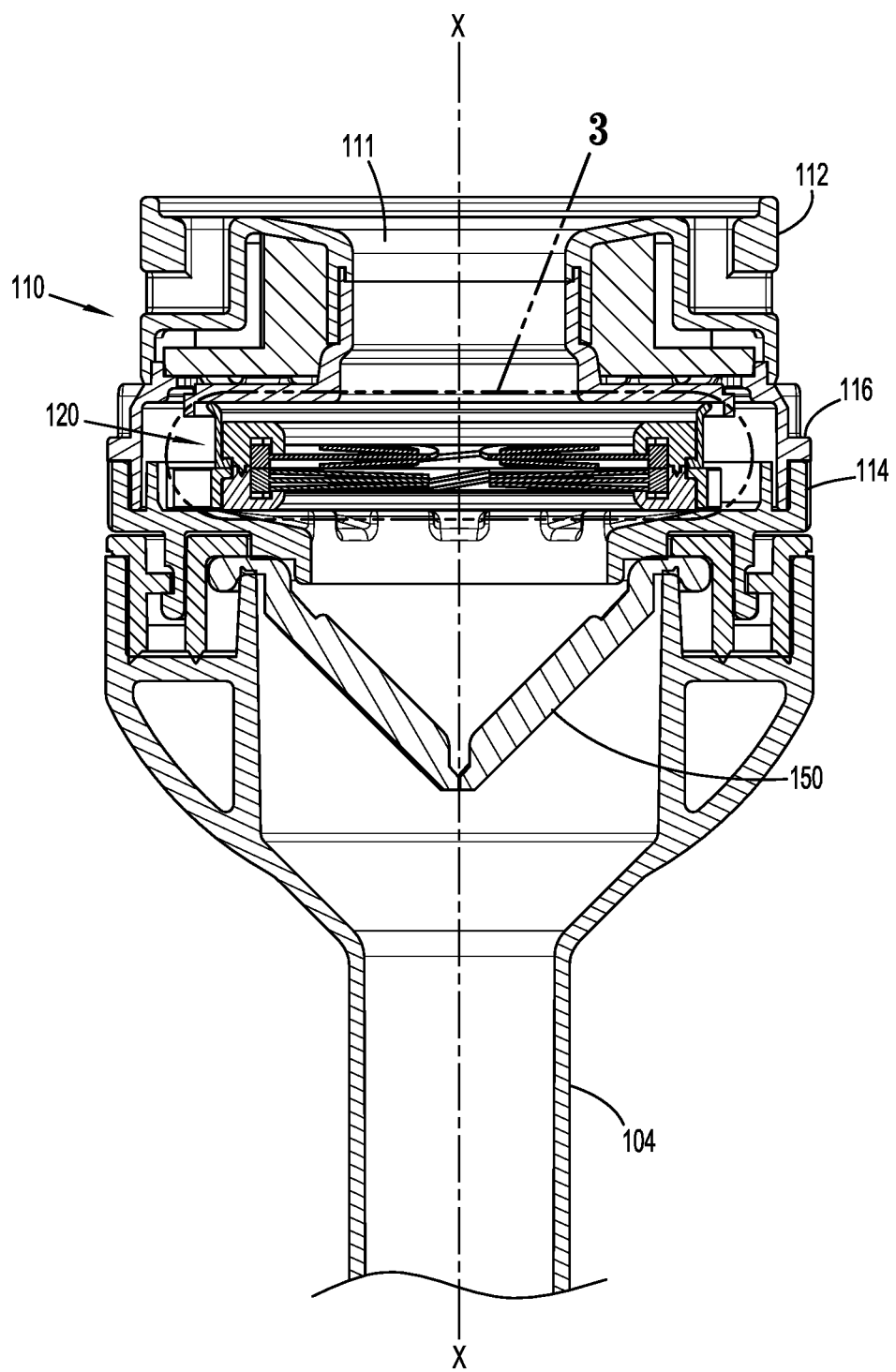
FIG. 2 is a cross-sectional view of the surgical access assembly of FIG. 1 taken along section line 2-2 of FIG. 1.

With additional reference to FIG. 2, the valve housing 110 of the surgical access assembly 100 includes an upper housing section 112, a lower housing section 114, and an inner housing section 116. The upper, lower, and inner housing sections 112, 114, 116 are configured to support a valve assembly 120 on a proximal end of the cannula 102. More particularly, the inner housing section 116 is secured between the upper and lower housing sections 112, 114, and the valve assembly 120 is received between the inner and lower housing sections 116, 114. The upper and lower housing sections 112, 114 of the valve housing 110 may be selectively attachable to, and detachable from, the inner housing section 116. The lower housing section 114 may be releasably or permanently attached to a cannula tube 104 of the cannula assembly 102. In embodiments, either or both of the upper and lower housing sections 112, 114 of the valve housing 110 may include knurls, indentations, tabs, or be otherwise configured to facilitate engagement by a clinician.

The surgical access assembly 100 may also include features for the stabilization of the surgical access assembly. For example, the distal end of the cannula tube 104 can carry a balloon anchor or another expandable member that engages the abdomen from the interior side. For example, see U.S. Pat. No. 7,300,448, the entire disclosure of which is hereby incorporated by reference herein. A feature on the opposite side of the abdominal wall can be used to further stabilize the surgical access assembly, such as adhesive tabs or adjustable foam collars.

The upper, lower, and inner housing sections 112, 114, 116 of the valve housing 110 define a longitudinal passage 111 for receipt of a surgical instrument (not shown). The valve assembly 120 is supported within the valve housing 110 to provide sealed passage of the surgical instrument through the surgical access assembly 100. A duck-bill or zero closure seal 150 is positioned in the valve housing 110. The zero closure seal 150 is configured to prevent fluids from passing from the cannula tube 104 and proximally through the valve housing 110 in the absence of a surgical instrument positioned in the valve housing 110.

Figure 3:
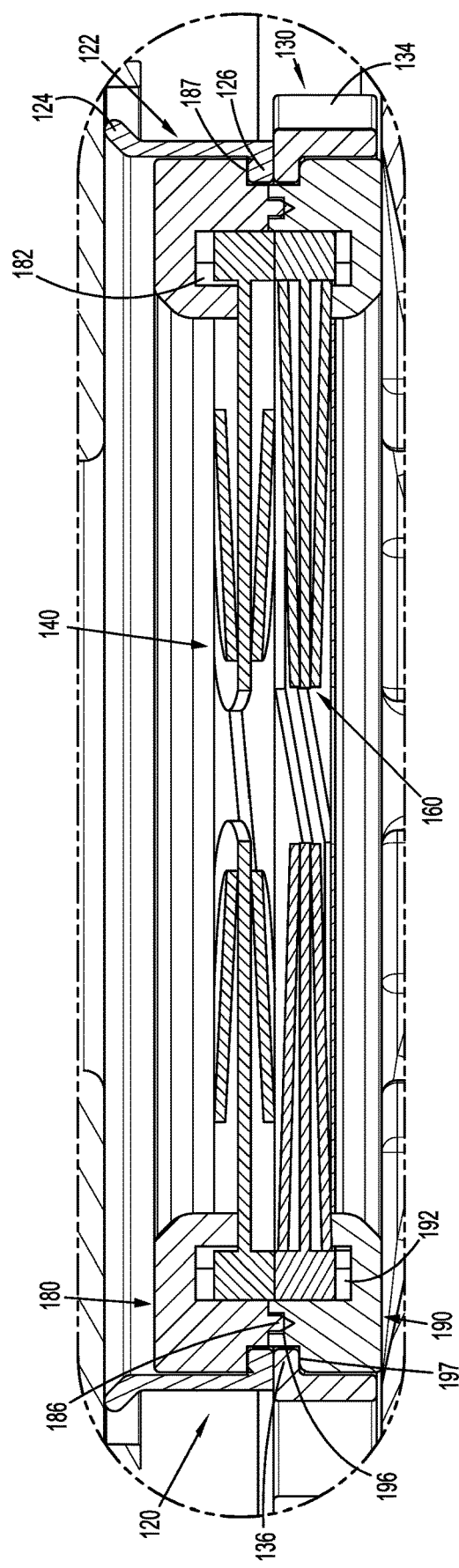
FIG. 3 is an enlarged view of the indicated area of detail of FIG. 2.
Figure 4:
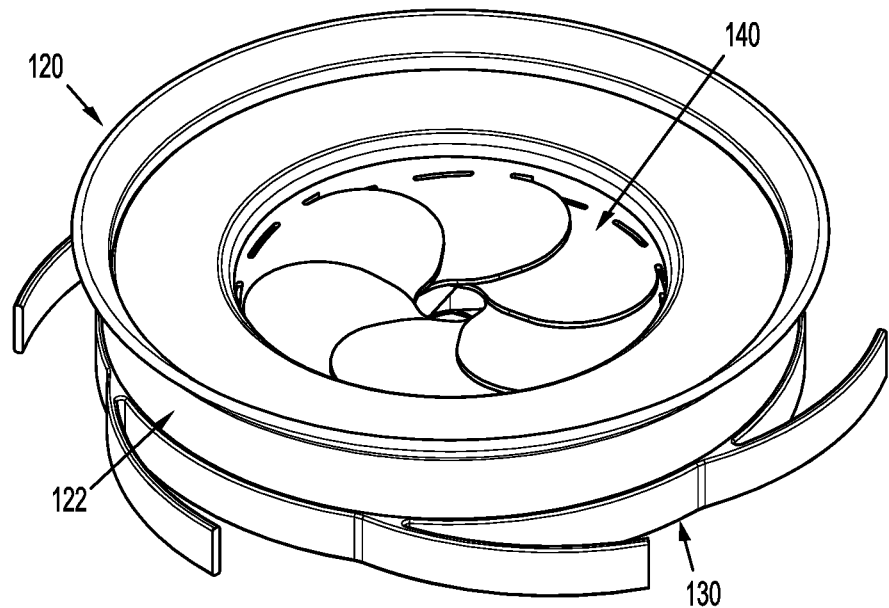
FIG. 4 is a top perspective view of a valve assembly according to an embodiment of the present disclosure.
Figure 5:
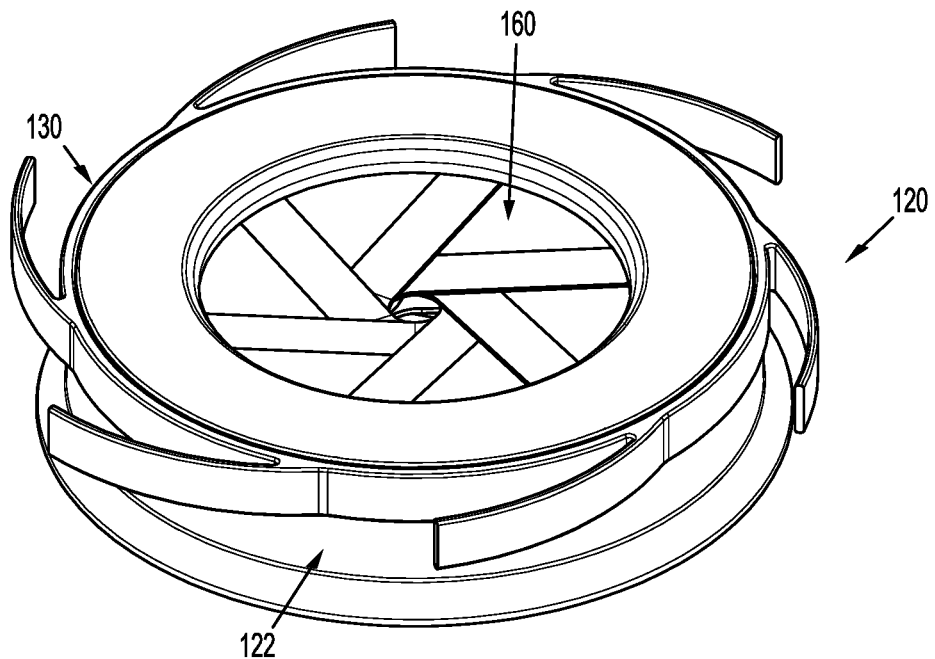
FIG. 5 is a bottom perspective view of the valve assembly of FIG. 4.

Referring now to FIG. 3, the various components of the valve assembly 120 are illustrated in their assembled configuration. The valve assembly 120 includes a ring 122, a centering mechanism 130, a guard 140, a seal 160, and first and second discs 180, 190 of a retainer 200 (FIG. 6).

Figure 6:
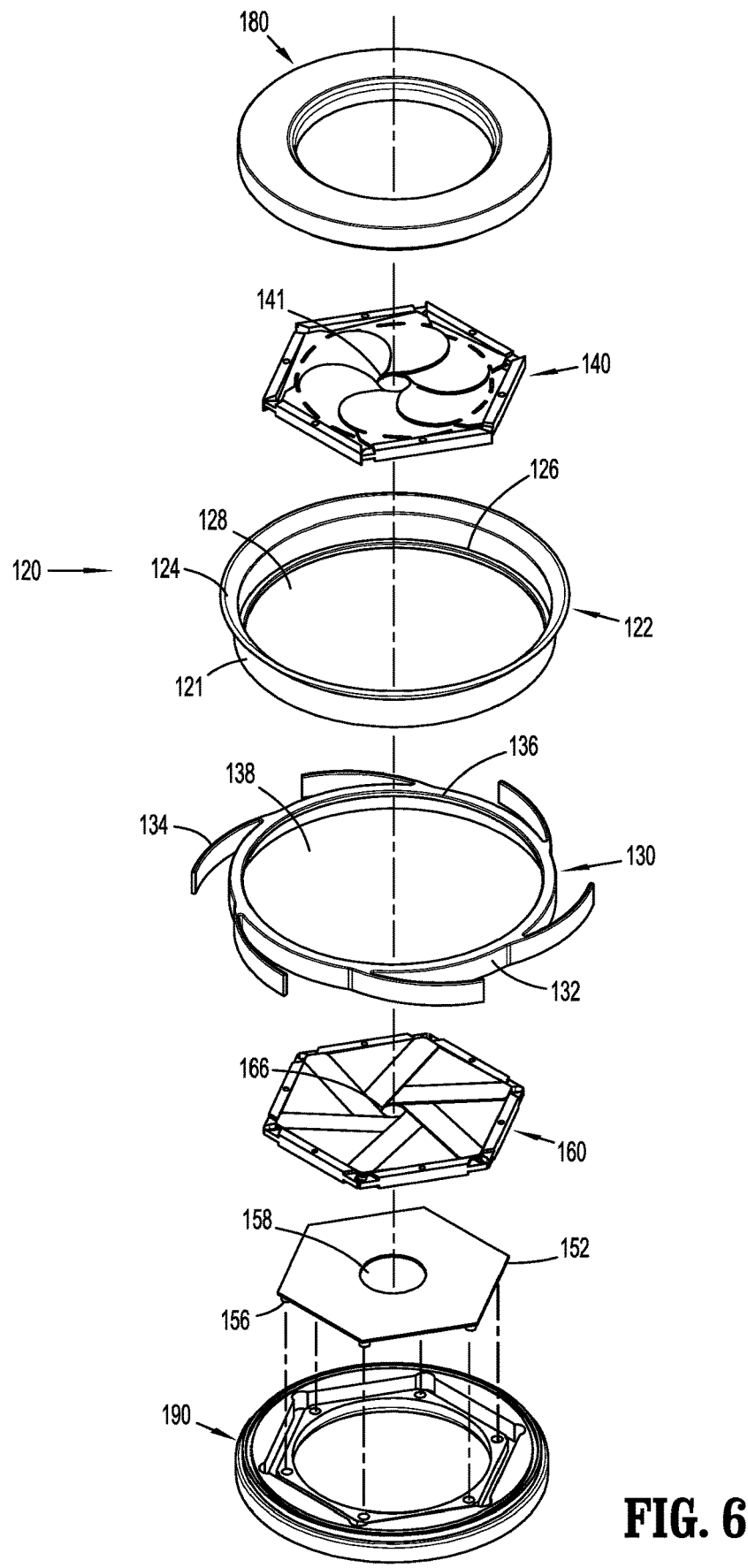
FIG. 6 is an exploded view, with parts separated, of the valve assembly of FIG. 4 including a centering mechanism, a ring, a guard, a seal, a plate, and a retainer.

With additional reference to FIG. 6, the ring 122 has a flange 124 and is located in a proximal region of the valve assembly 120. The flange 124 extends away from the ring 122 in a proximal direction and at an angle relative to the ring 122 such that a proximal end of the ring 122 has a diameter that is greater than a diameter of the distal end of the ring 122. A rim 126 extends towards a center opening 128 of the ring 122 (i.e., inboard) from a distal end of a wall 121 of the ring 122 and defines a ledge. The rim 126 is in an abutting relationship with a hoop 132 of the centering mechanism 130.

With continued reference to FIGS. 1-3 and 6, the centering mechanism 130 includes the hoop 132 and fingers 134 that are flexibly and resiliently attached to an outer surface of the hoop 132. The fingers 134 extend radially from the outer surface of the hoop 132 and are biased away from the outer surface of the hoop 132. When the centering mechanism 130 is disposed in the valve housing 110, distal portions of the fingers 134 are in contact with an inner surface of the lower housing section 114. The fingers 134 are configured to help maintain a center of the hoop 132 in coaxial alignment with a central longitudinal axis X-X of the valve housing 110. The hoop 132 is spring loaded when positioned in the valve housing 110 as all of the fingers 134 are slightly compressed towards the outer surface of the hoop 132. As the fingers 134 are compressed equally, the hoop 132 is in a state of equilibrium and its center is coaxially aligned with the central longitudinal axis X-X of the valve housing 110. When the hoop 132 is moved radially away from the central longitudinal axis X-X of the valve housing 110, some of the fingers 134 are compressed to a greater extent and some of the fingers 134 are under less compression (i.e., relaxed). This can occur when a surgical instrument is inserted through the hoop 132 and moved radially with respect to the central longitudinal axis X-X of the valve housing 110. Once the surgical instrument is removed, the fingers 134 under greater compression urge the hoop 132 back towards the central longitudinal axis X-X and towards the state of equilibrium. Additionally, the hoop 132 includes a rim 136 that extends towards an opening 138 of the hoop 132 (i.e., inboard) from a proximal end of a wall of the hoop 132 and defines a ledge. The rim 136 of the hoop 132 is in an abutting relationship with the rim 126 of the ring 122. The rim 136 of the hoop 132 and the rim 126 of the ring 122 both extend the same distance inboard.

Referring now to FIGS. 3, 7, 11, and 15, the first disc 180 and the second disc 190 of the retainer 200 are securable to each other. The first or top disc 180 has a central opening 188 and a ridge 186 that circumscribes the central opening 188. A recess 183 extends beneath a bottom surface of the first disc 180. Although shown as a hexagonal recess 183, it is contemplated that the recess 183 may have a different configuration with fewer (e.g., 4) sides or with more (e.g., 8) sides to match the configuration of the guard 140. Continuing with the hexagonal configuration, each side of the recess 183 includes a channel 182 that is configured to receive a portion of a frame 148 of the guard 140. In particular, the frame 148 includes a complementary number of sides 144a-f and each side 144a-f is insertable into one of the channels 182. This arrangement fixes the orientation between the first disc 180 and the guard 140 such that the guard 140 remains rotationally fixed relative to the first disc 180 as the sides 144a-f of the frame 148 are at least partially inserted into the channels 182 of the recess 183. The second or bottom disc 190 has a slot 196 that is configured to receive the ridge 186 of the first disc 180 therein. The second disc 190 also includes a hexagonal depression 193 that extends beneath a top surface of the second disc 190. Similar to the first disc 180, the second disc 190 may have a configuration with fewer sides or more sides and this configuration need not match the configuration of the first disc 180, but does match the configuration of a support 170 of the seal 160. Continuing with the hexagonal configuration, each side of the depression 193 includes a groove 192 that is configured to receive a portion of the support 170 of the seal 160. In particular, the support 170 includes a complementary number of sides 172a-f and each side 172a-f is insertable into one of the grooves 192. This arrangement fixes the orientation between the second disc 190 and the seal 160 such that seal 160 remains rotationally fixed relative to the second disc 190 as the sides 172a-f of the support 170 are at least partially inserted into the grooves 192 of the depression 193. Additionally, the depression 193 includes receptacles 194 that are configured to accept protrusions 156 of a plate 152 (FIG. 6). The engagement between the protrusions 156 of the plate 152 and the receptacles 194 of the second disc 190 couple the plate 152 to the second disc 190 and maintains a fixed orientation between them. By using protrusions 156 on the plate 152 and receptacles 194 in the second disc 190, the orientation between the plate 152 and the second disc 190 is limited to a fixed number of orientations. The plate 152 helps support the seal 160 and limits the flexion of petals 162a-f of the seal 160 towards the cannula tube 104 when a surgical instrument (not shown) is inserted through the seal degrees.

Referring now to FIGS. 3, 4, 6, and 15, the guard 140 includes the frame 148 that has six sides 144a-f. As described hereinabove, the frame 148 may include fewer sides (e.g., 4) or more sides (e.g., 8) provided that the number of sides 144 corresponds to the number of channels 182 in the first disc 180. Each side 144a-f includes a bar 145a-f that is generally rectangular and extends along a majority of a length of the corresponding flap 142a-f. Each block 146a-f extends from one end of the bar 145a-f of the corresponding side 144a-f. Each block 146a-f is positioned midway between top and bottom surfaces of the bar 145a-f and extends parallel to the top and bottom surfaces of the bar 145a-f. Each bar 145a-f is configured to be received in the corresponding channel 182 of the recess 183 of the first disc 180 thereby fixing the relative orientations of the guard 140 with respect to the first disc 180. As assembled, the bottom surfaces of the bars 145a-f are substantially flush with a bottom surface of the first disc 180. Further, with the guard 140 positioned in the recess 183 of the first disc 180, the first disc 180 is disposed in the center opening 128 of the ring 122.

Figure 8:
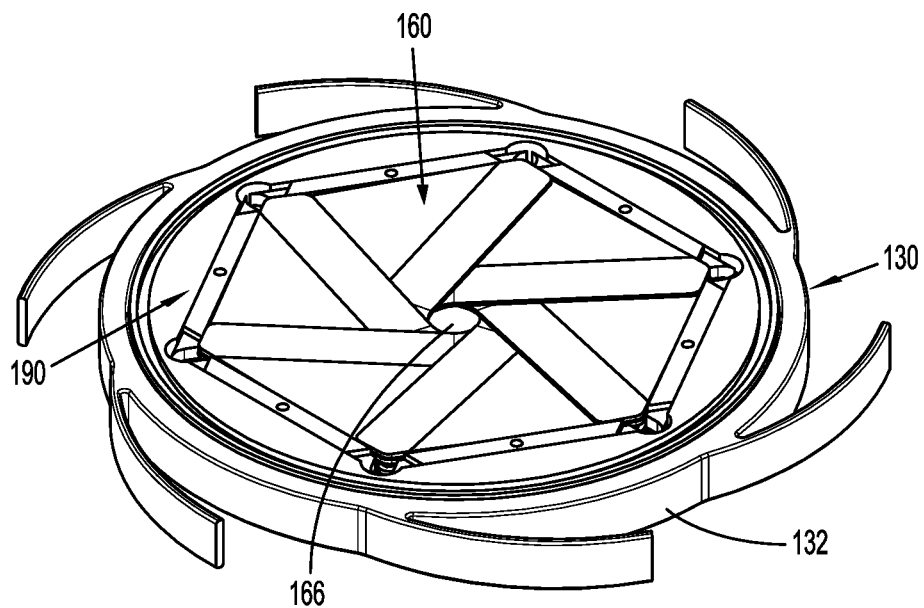
FIG. 8 is a top perspective view of the seal of FIG. 6 disposed in the bottom disc of the retainer of FIG. 6 and the bottom disc is disposed in a hoop of the centering mechanism of FIG. 6.
Figure 11:
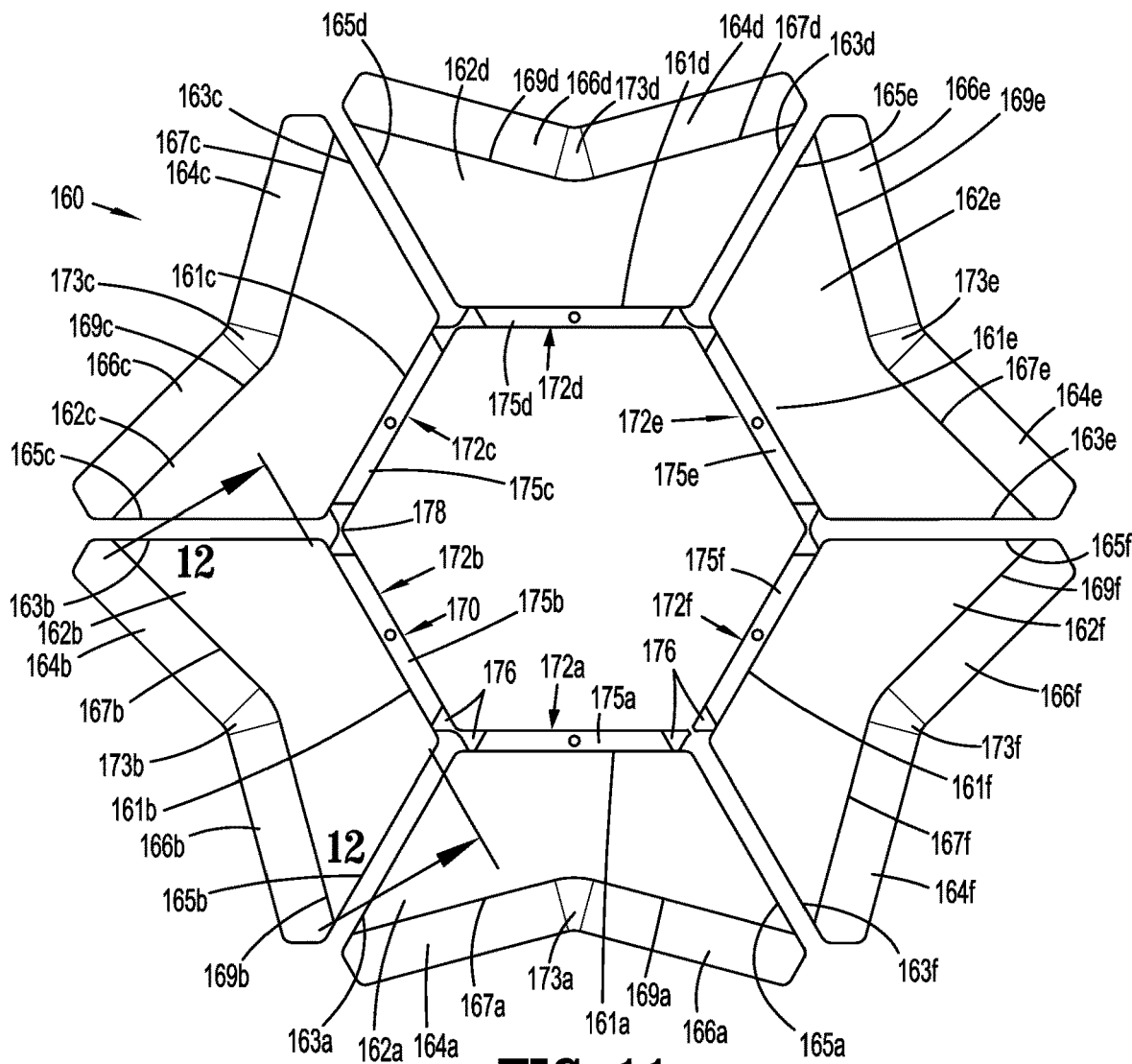
FIG. 11 is a top plan view of the seal of FIG. 10.

With additional reference to FIGS. 8 and 11, the seal 160 is illustrated with a support 170 having six sides 172a-f. As described hereinabove, the support 170 may include fewer sides (e.g., 4) or more sides (e.g., 8) provided that the number of sides 172 corresponds to the number of grooves 192 in the second disc 190. Each side 172a-f includes a beam 175a-f that is generally rectangular and extends along a majority of a length of the corresponding petal 162a-f. Wedges 176 extend from opposing ends of each beam 175a-f. Each wedge 176 is positioned midway between top and bottom surfaces of the beam 175a-f and extends parallel to the top and bottom surfaces of the beam 175a-f. As will be described in further detail below, the wedges 176 are joined to form living hinges 178. Each beam 175a-f is configured to be received in the corresponding groove 192 of the depression 193 of the second disc 190 thereby fixing the relative orientations of the seal 160 with respect to the second disc 190. As assembled, the top surfaces of the beams 175a-f are substantially flush with a top surface of the second disc 190. Further, with the seal 160 positioned in the depression 193 of the second disc 190, the second disc 190 is disposed in the opening 138 of the hoop 132.

Figure 7:
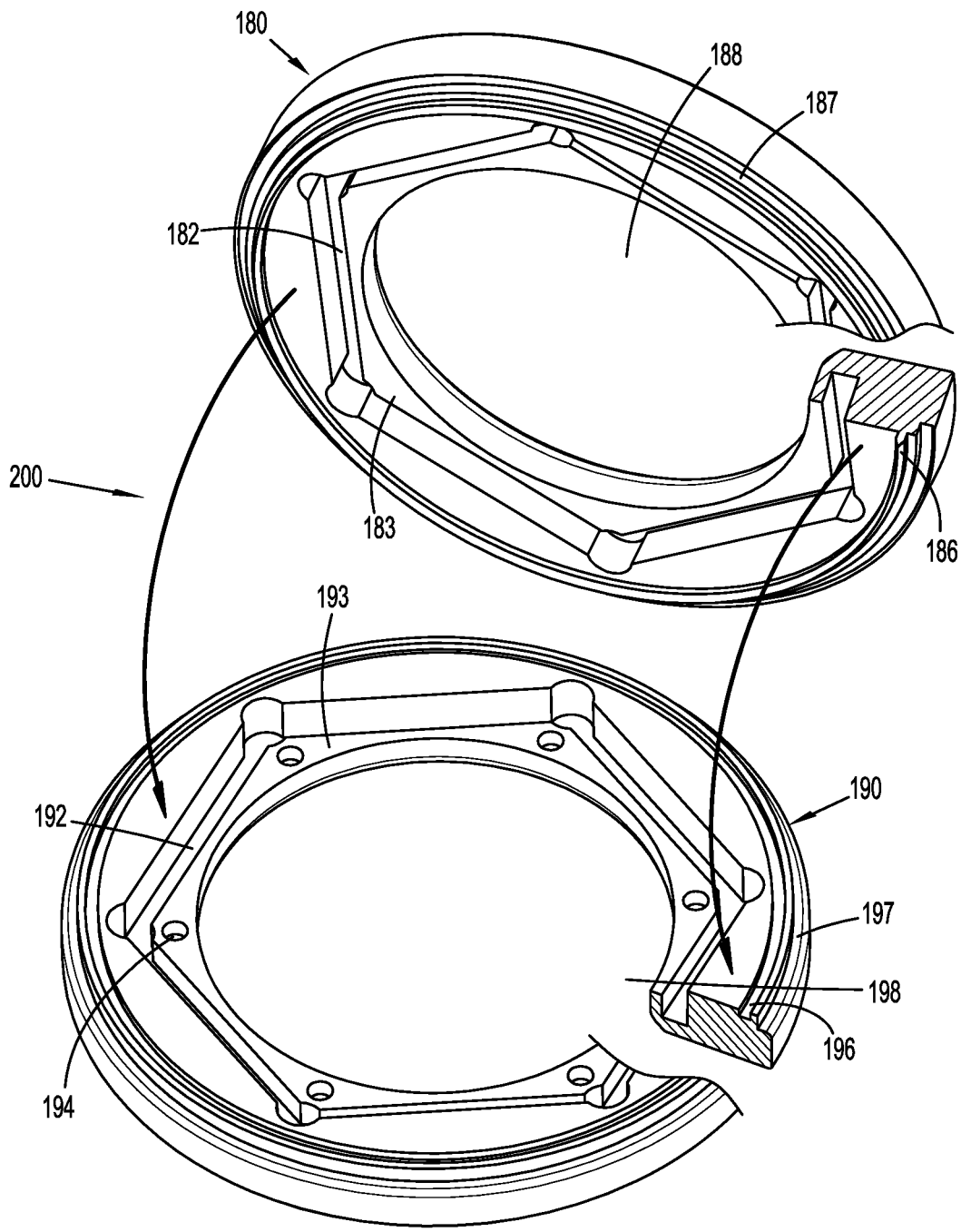
FIG. 7 is a bottom perspective view of a top disc of the retainer of FIG. 6 and a top perspective view of a bottom disc of the retainer of FIG. 6.
Figure 9:
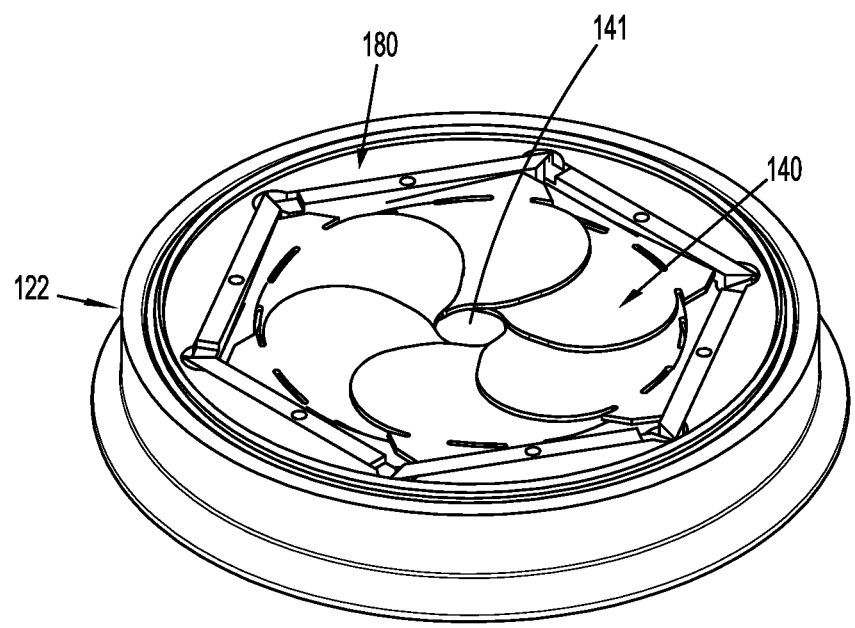
FIG. 9 is a bottom perspective view of the guard of FIG. 6 disposed in the top disc of the retainer of FIG. 6 and the top disc is disposed in the ring of FIG. 6.

Referring now to FIGS. 3, 8, and 9, the first disc 180 with the guard 140 installed therein is positioned in the ring 122 and the second disc 190 with the seal 160 installed therein is positioned in the hoop 132. As seen in FIGS. 3 and 7, the first disc 180 has a notch 187 at its distal end that circumscribes the first disc 180. The notch 187 is configured to complement the rim 126 of the ring 122 and support the first disc 180 in the opening 128 of the ring 122. The rim 126 provides a limit stop on movement of the first disc 180 through the ring 122 in a distal direction. It is contemplated that an outer diameter of the first disc 180 and an inner diameter of the ring 122 may be sized such that the first disc 180 is retained within the opening 128 of the ring 122 by frictional engagement between the outer surface of the first disc 180 and an inner surface of the ring 122. Similarly, the second disc 190 also includes a notch 197 at its proximal end that circumscribes the second disc 190. The notch 197 is configured to complement the ledge 136 of the hoop 132 and limit the proximal travel of the second disc 190 through the hoop 132. It is contemplated that an outer diameter of the second disc 190 and an inner diameter of the hoop 132 may be sized such that the second disc 190 is retained within the hoop 132 by frictional engagement between the outer surface of the second disc 190 and an inner surface of the hoop 132. With the first disc 180 fully seated in the ring 122 and the second disc 190 fully seated in the hoop 132, placing the ring 122 and the hoop 132 are in an abutting relationship results in the bottom surface of the first disc 180 resting atop the top surface of the second disc 190. Further still, the ridge 186 that extends from the bottom surface of the first disc 180 enters the slot 196 that extends into the top surface of the second disc 190, thereby coupling the first and second discs 180, 190 as well as the ring 122 and the hoop 132.

As the ridge 186 of the first disc 180 and the slot 196 of the second disc 190 extend continuously around central openings 188, 198 of the respective first and second discs 180, 190, the first disc 180 can be attached to the second disc 190 in a multitude of orientations rather than a discrete number of orientations that would be defined by a complementary arrangement of posts and receptacles as seen with the fixation arrangement of the plate 152 and the second disc 190. Additionally, by using the ridge 186 and slot 196 arrangement between the first and second discs 180, 190, the orientation between the guard 140 and the seal 160 is easily adjustable prior to securing the first and second discs 180, 190 together. This simplifies the assembly of the valve assembly 120 and assists in orienting the guard 140 and seal 160 prior to securing the first and second discs 180, 190 together. Once the desired orientation between the guard 140 and seal 160 is achieved, the first disc 180 is welded to the second disc 190. Welding the first and second discs 180, 190 together provides a fluid tight seal between the first and second discs 180, 190. It is contemplated that the first and second discs 180, 190 may be secured to each other using an adhesive. It is also contemplated that the first disc 180 may include a slot and the second disc 190 may include a ridge.

Figure 10:
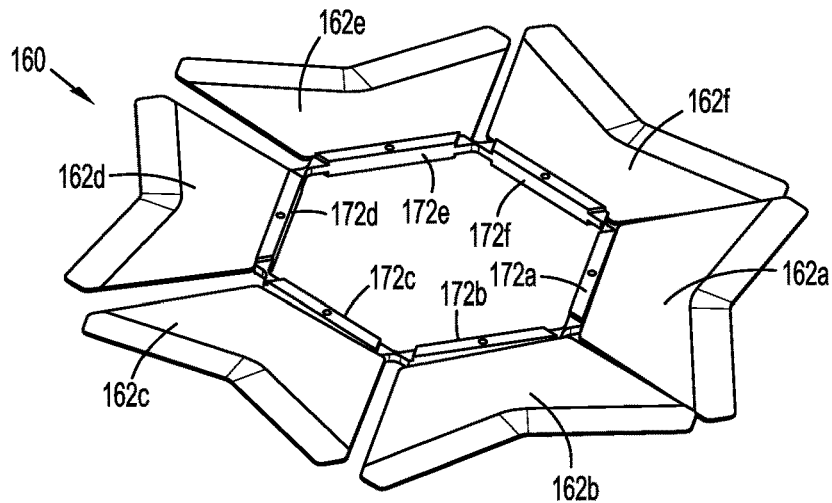
FIG. 10 is a top perspective view of the seal of FIG. 6 in an unfolded configuration.
Figure 12:
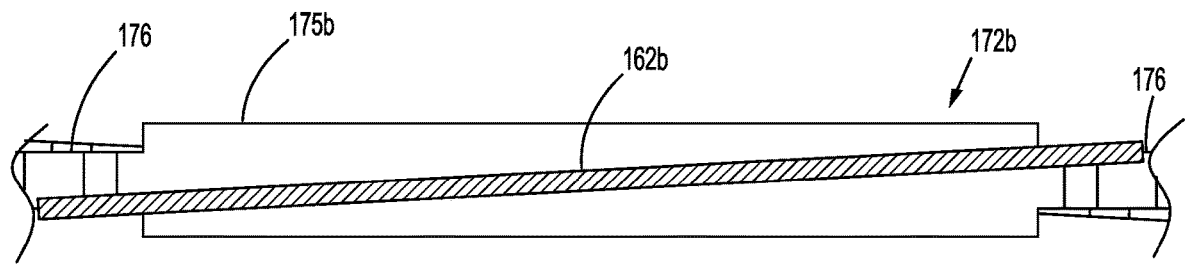
FIG. 12 is an end cross-sectional view of a petal of the seal taken along section line 12-12 of FIG. 11.
Figure 13:
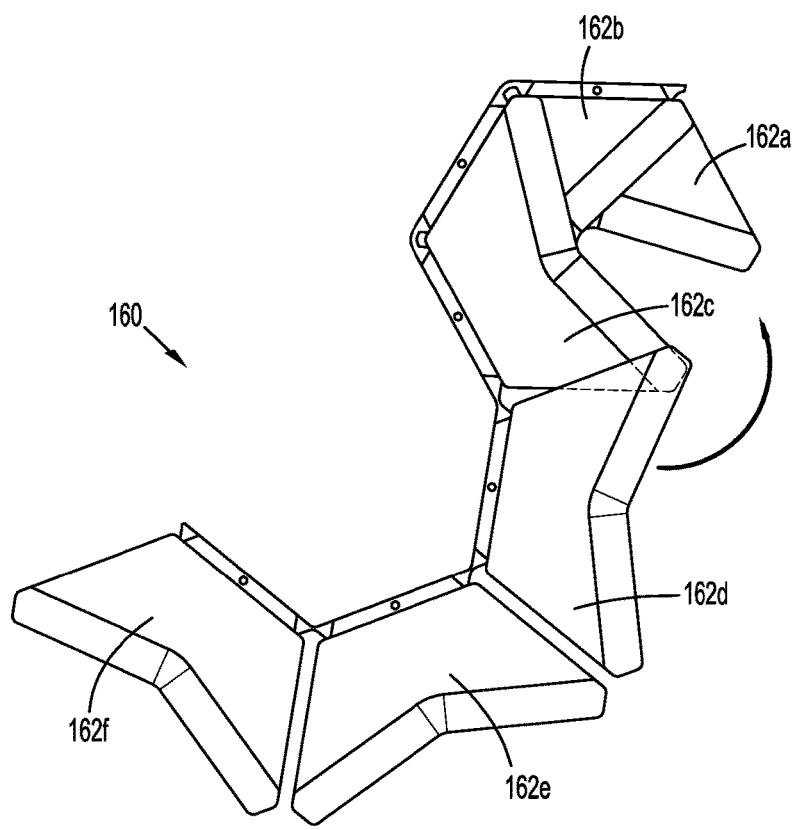
FIG. 13 is a top plan view of the seal of FIG. 10 showing the folding sequence of the petals.

Referring now to FIGS. 10-14, the sequence of steps for transforming the seal 160 from an unfolded configuration (FIG. 10) to a folded configuration (FIG. 14) is illustrated. Initially, as seen in FIGS. 10 and 11, the seal 160 is in the unfolded configuration. Each beam 175a-f is connected to an adjacent beam 175a-f with one exception. As shown in FIG. 11, one of the wedges 176 of the first petal 162a is spaced apart from one of the wedges of the sixth petal 162f defining a gap therebetween while the remaining wedges 176 are connected to each other. A living hinge 178 is formed where the wedges 176 are connected to each other. Additionally, as seen in FIG. 12, each petal 162a-f is angled with respect to the top and bottom surfaces of the corresponding beam 175a-f. This angled arrangement in conjunction with the gap between the wedges 176 of the first and sixth petals 162a, 162f facilitates folding and unfolding of the seal 160 as will be discussed hereinbelow. Each petal 162a-f is connected to a corresponding beam 175a-f of the support 170 along a first or connection side 161a-f. Each petal 162a-f also includes angled second and third sides 163a-f, 165a-f that extend from the corresponding connection side 161a-f in a divergent manner. Fourth and fifth sides 167a-f, 169a-f of each petal 162a-f interconnect the angled second and third sides 163a-f, 165a-f. The fourth and fifth sides 167a-f, 169a-f of the petals 162a-f have equal lengths and are angled towards the corresponding connection side 161a-f such that they meet at a point that would bisect the connection side 161a-f. The fourth and fifth sides are oriented such that they that they define an angle of 150°. The fourth and fifth sides may define an angle between about 120° and about 165°. First and second extenders 162a-f, 164a-f are attached to the fourth and fifth sides 167a-f, 169a-f. The first and second extenders 162a-f, 164a-f have equal lengths and meet at a taper 173a-f that also is located at a point that would bisect the corresponding connection side 161a-f.

Figure 14:
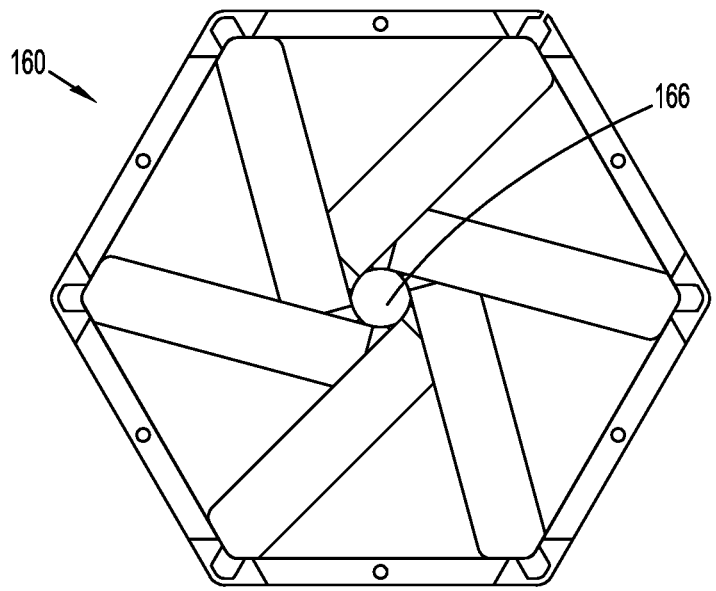
FIG. 14 is a top plan view of the seal of FIG. 10 in a fully folded configuration.

The wedges 176 of the first through fifth beams 175a-e are connected to the wedges 176 of the second through sixth beams 175b-f defining five living hinges 178 with a gap existing between the first beam 175a and the sixth beam 175f. Since the wedge 176 of the first beam 175a is not connected to the wedge 176 of the sixth beam 175f, the first beam 175a and the first petal 162a can be repositioned without disturbing the position of the sixth beam 175f and the sixth petal 162f. The first petal 162a is folded by pivoting the first beam 175a and the first petal 162a about a point defined by the living hinge 178 that is disposed between the first and second beams 175a, 175b. As such, the first petal 162a partially overlaps the second petal 162b. Subsequently, the first and second petals 162a, 162b are pivoted by pivoting the second beam 175b about the living hinge 178 formed between the second beam 175b and the third beam 175c such that the second petal 162b partially overlaps the third petal 162c. Next, the first, second, and third petals 162a-c are pivoted by pivoting the third beam 175c about the living hinge 175 formed between the third beam 175c and the fourth beam 175d such that the third petal 162c partially overlaps the fourth petal 162d. Subsequently, the first, second, third, and fourth petals 162a-d are pivoted by pivoting the fourth beam 175d about the living hinge 178 formed between the fourth beam 175d and the fifth beam 175e such that the fourth petal 162d partially overlaps the fifth petal 162e. The first, second, third, fourth, and fifth petals 162a-e are pivoted by pivoting the fifth beam 175e about the living hinge 178 formed between the fifth beam 175f and the sixth beam 175f such that the fifth petal 162e partially overlaps the sixth petal 162f and the sixth petal 162f partially overlaps the first petal 162a. The fully folded seal 160 is illustrated in FIG. 14.

After all the petals 162a-f are folded, a center orifice 166 is defined and is configured to engage an outer surface of a surgical instrument inserted through the seal 160 such that the center orifice 166 surrounds the surgical instrument in a sealing manner to inhibit the passage of insufflation fluids and define a fluid tight barrier. As each petal 162a-f at least partially overlaps a first adjacent petal 162 and is at least partially overlapped by a second adjacent petal 162, the petals 162a-f of the seal are interwoven. This interwoven arrangement of the petals 162a-f facilitates the seal 160 maintaining its shape during insertion and withdrawal of a surgical instrument through the center orifice 166. For example, with additional reference to FIGS. 2 and 3, during insertion of the surgical instrument through the valve housing 110 of the surgical access assembly 100, a shaft of the surgical instrument passes through the central opening 188 of the first disc 188, a center bore 141 of the guard 140, the center orifice 166 of the seal 160, and the central opening 198 of the second disc 190. As the shaft of the surgical instrument passes through the center orifice 166 of the seal 160 during insertion, the petals 162a-f of the seal 160 flex towards the second disc 190 and surround an outer surface of the shaft of the surgical instrument providing a fluid tight barrier between the petals 162a-f of the seal 160 and the shaft of the surgical instrument. During withdrawal of the surgical instrument, the petals 162a-f of the seal 160 flex towards a proximal portion of the valve housing 110 in response to proximal movement of the shaft of the surgical instrument. The petals 162a-f of the seal 160 resiliently return to their initial or rest configuration (FIG. 3) once the shaft of the surgical instrument is removed from the center orifice 166 of the seal 160. Due to the petals 162a-f being interwoven, they return to the initial configuration. In the event that the petals 162a-f have slightly different rates of movement, the interwoven arrangement of the petals 162a-f results in the slowest moving petal 162 acting as a governor and limiting the rate of movement of the remaining petals 162. This tends to maintain contact between the petals 162a-f and the outer surface of the shaft of the surgical instrument thereby maintaining the fluid tight boundary of the seal 160 with respect to the surgical instrument during movement of the shaft relative to the seal 160.

Referring now to FIGS. 15-18, the guard 140 of the valve assembly 120 is illustrated. The guard 140 helps protect the seal 160 during insertion and withdrawal of the surgical instrument through the valve assembly 120. The central opening 141 of the guard 140 has a diameter that is greater than the outer diameter of the shaft of the surgical instrument. During insertion of the surgical instrument through the valve assembly 120, the shaft of the surgical instrument passes through the central opening 141 of the guard 140. As the diameter of the central opening 141 is greater than the diameter of the shaft of the surgical instrument, the shaft may pass through the central opening 141 without contacting any flaps 142a-f of the guard 140. In instances where the shaft is off axis from a central longitudinal axis of the guard 140 or the shaft is inserted at an angle relative to the central longitudinal axis, the tip of the shaft contacts one or more flaps 142a-f of the guard 140 as the shaft moves through the central opening 141 of the guard 140. The central longitudinal axis of the guard 140 is coaxially aligned with the central longitudinal axis X-X of the valve housing 110 (FIG. 2). The flap or flaps 142a-f of the guard 140 act to reduce any impact force from the tip of the shaft that would be transmitted to the seal 160. This helps maintain the integrity and lifespan of the seal 160 such that the seal 160 is capable of enduring multiple insertions of the surgical instrument without damage from the surgical instrument.

Figure 15:
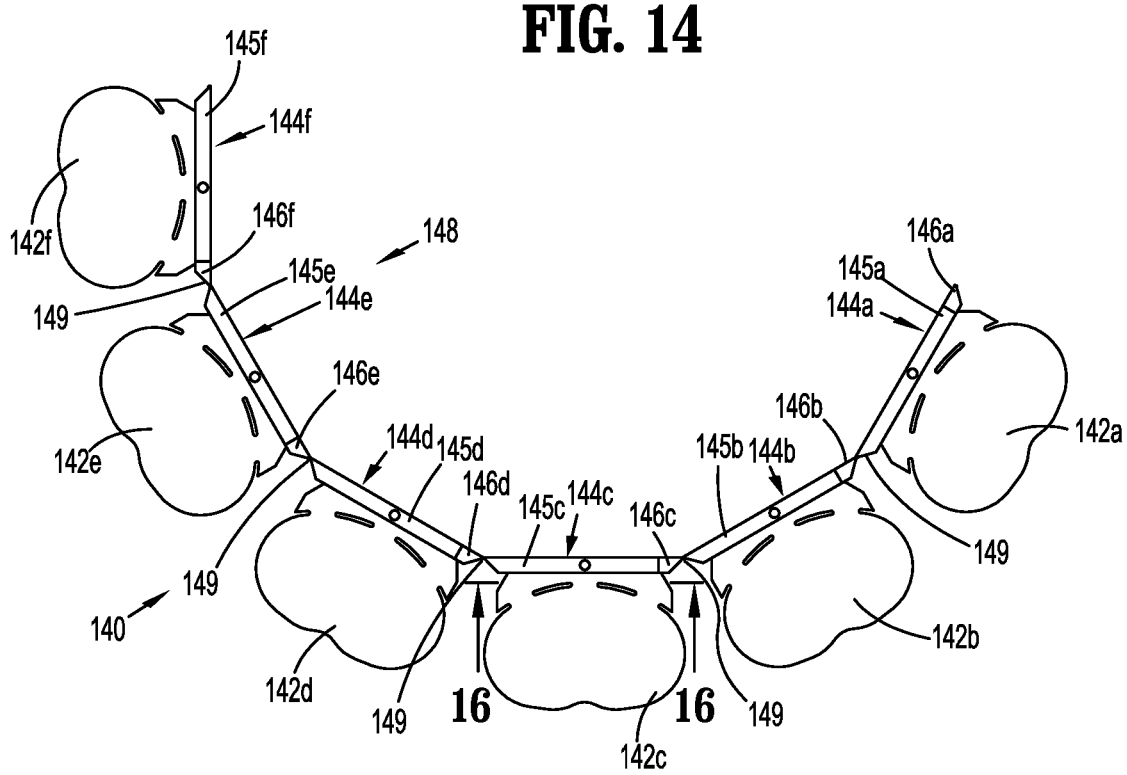
FIG. 15 is a top plan view of the guard of FIG. 6 in an unfolded configuration.
Figure 16:
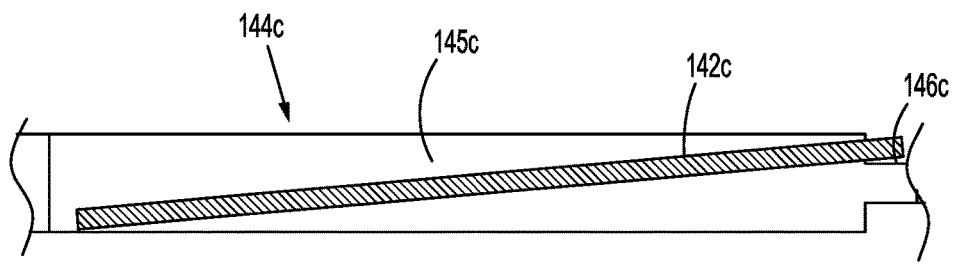
FIG. 16 is an end cross-sectional view of a flap of the guard taken along section line 16-16 of FIG. 15.
Figure 17:
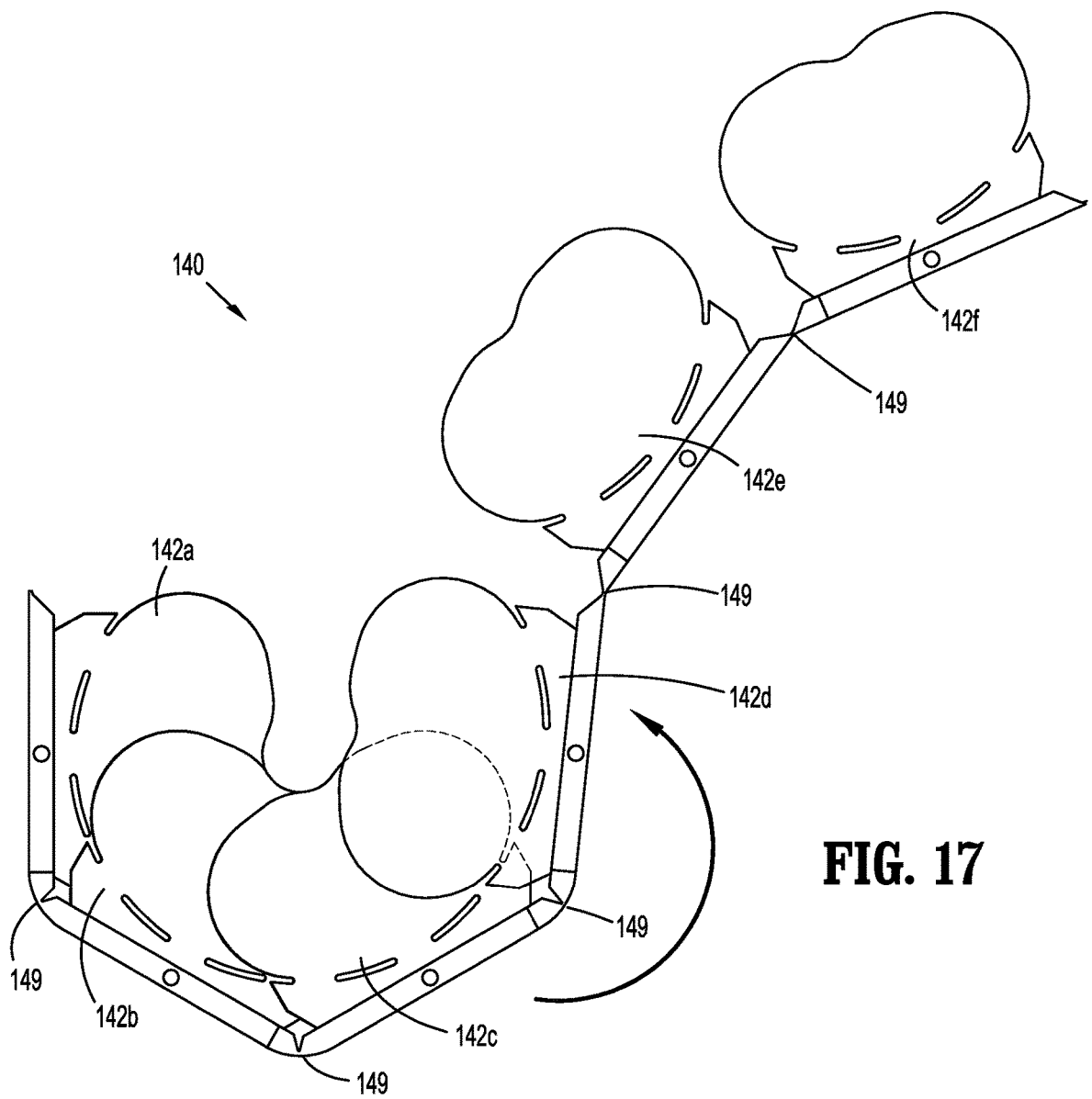
FIG. 17 is a top plan view of the guard of FIG. 15 showing the folding sequence of the flaps.

In particular, the guard 140 includes the flaps 142a-f that are attached to a multi-sided frame 148. As illustrated in FIG. 15, the guard 140 includes a six-sided frame 148 with six flaps 142a-f where each flap 142a-f is flexibly and resiliently attached to one side 145a-f of the frame 148. The frame 148 may include fewer sides 145 (e.g., 4) or more sides 145 (e.g., 8) provided that the number of sides 145 corresponds to the number of channels 182 present in the recess 183 of the first disc 180. Each side 145a-f of the frame 148 is a generally trapezoidal configuration. Similar to the support 170 of the seal 160, the sides 145-a-f of the frame 148 are joined to one another with the exception of two of the sides 145a, 145f (FIG. 15). Each side 145a-f of the frame 148 has a block 146a-f at one end of the side 14a-f. The blocks 146a-e of the first through fifth sides 145a-e are connected to the second through sixth sides 145b-f defining five living hinges 149. Since the block 146a of the first side 145a is not connected to the sixth side 145f, the first side 145a and the first flap 142a can be repositioned without disturbing the position of the sixth side 145f and the sixth flap 142f. This allows folding of the guard 140 as will be explained hereinbelow. Additionally, as seen in FIG. 16, each flap 142a-f is angled with respect to the top and bottom surfaces of the corresponding side 145a-f. This angled arrangement in conjunction with the gap between the first side 145a and the sixth side 145f facilitates folding and unfolding of the guard 140 as will be discussed hereinbelow.

Figure 18:
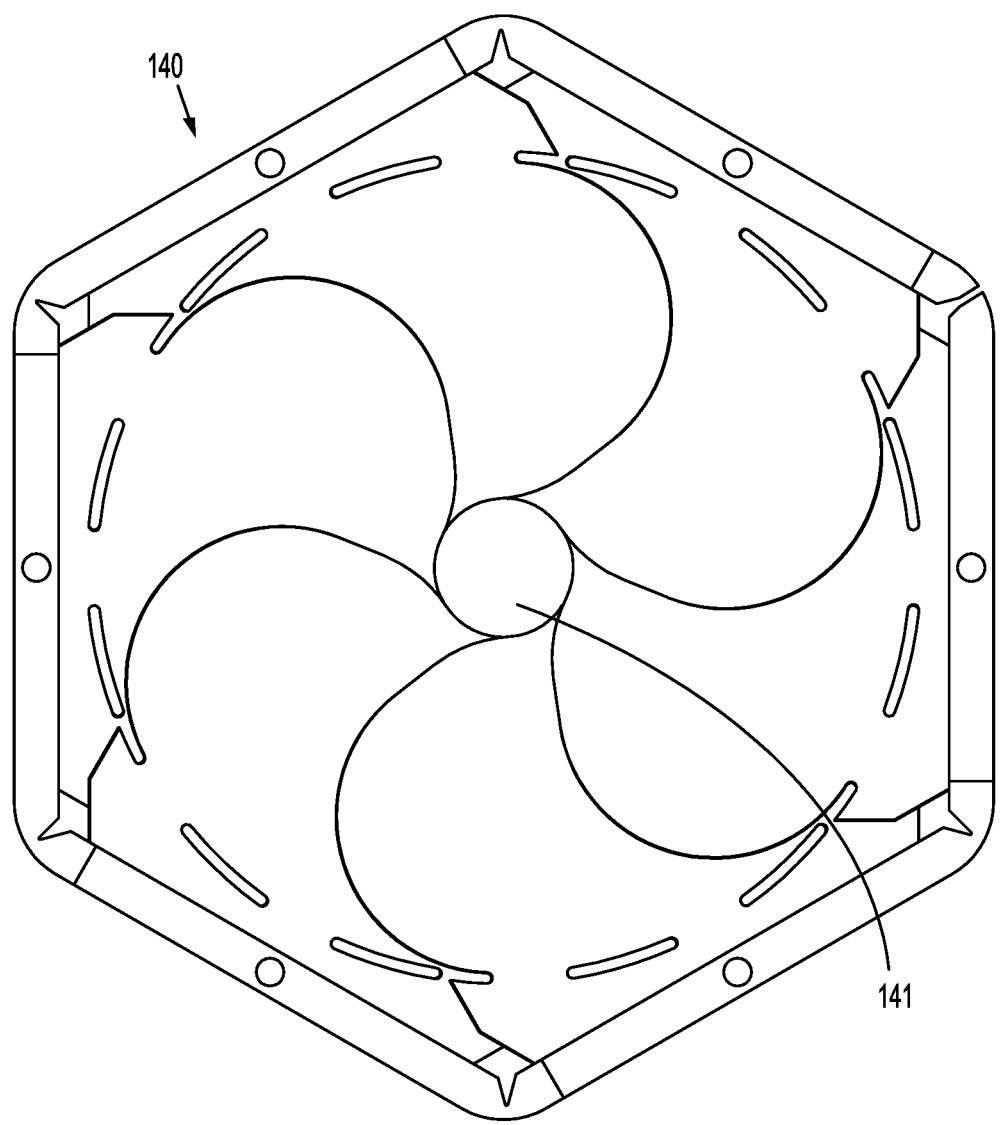
FIG. 18 is a top plan view of the guard of FIG. 15 in a fully folded configuration.

With the guard 140 in an initial, unfolded configuration (FIG. 15), the first flap 142a is folded by pivoting the first side 145a and the first flap 142a about a point defined by the living hinge 149 that is disposed between the first and second sides 145a, 145b. As such, the first flap 142a partially overlaps the second flap 142b. Subsequently, the first and second flaps 142a, 142b are pivoted by pivoting the second side 145b about the living hinge 149 formed between the block 146b of the second side 145b and the third side 145c such that the second flap 142b partially overlaps the third flap 142c. Next, the first, second, and third flaps 142a-c are pivoted by pivoting the third side 145c about the living hinge 149 formed between the block 146c of the third side 145c and the fourth side 145d such that the third flap 142c partially overlaps the fourth flap 142d. Subsequently, the first, second, third, and fourth flaps 142a-d are pivoted by pivoting the fourth side 145d about the living hinge 149 formed between the block 149d of the fourth side 145d and the fifth side 145e such that the fourth flap 142d partially overlaps the fifth flap 142e. The first, second, third, fourth, and fifth flaps 142a-e are pivoted by pivoting the fifth side 145e about the living hinge 149 formed between the block 146e of the fifth side 145e and the sixth side 145f such that the fifth flap 142e partially overlaps the sixth flap 142f and the sixth flap 142f partially overlaps the first flap 142a. The fully folded guard 140 is illustrated in FIG. 18.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. A surgical access assembly comprising:
   a cannula;
   a valve housing coupled to a proximal end of the cannula; and
   a valve assembly disposed in the valve housing, the valve assembly including:
      a centering mechanism including a hoop having fingers extending radially outwards from an outer surface of the hoop, each finger being flexibly connected to the outer surface and biased away from the outer surface, the hoop having a ledge;
      a ring with an outer diameter and a flange disposed at one end of the ring, the other end of the ring abutting the ledge;
      a retainer having a first disc disposed in the ring and a second disc disposed in the hoop, the first disc attachable to the second disc irrespective of a rotational orientation of the first disc relative to the second disc;
      a guard including a frame and flaps flexibly coupled thereto, the frame partially disposed in a channel of the first disc; and
      a seal including petals flexibly coupled to a support, the support partially disposed in a groove of the second disc such that the frame and the support abut one another.

2. The surgical access assembly of claim 1, wherein the second disc includes receptacles that are configured to receive protrusions of a plate.

3. The surgical access assembly of claim 1, wherein one of the first or second discs includes a ridge circumscribing a central opening thereof and the other of the first or second discs includes a slot circumscribing a central opening thereof, the ridge adapted to fit within the slot thereby coupling the first and second discs.

4. The surgical access assembly of claim 3, wherein the first disc is secured to the second disc.

5. The surgical access assembly of claim 3, wherein the first disc is welded to the second disc.

6. The surgical access assembly of claim 1, wherein the frame is positionable in the channel such that the guard has a fixed rotation relationship with the first disc.

7. The surgical access assembly of claim 1, wherein the support is positionable in the groove such that the seal has a fixed rotational relationship with the second disc.

8. A surgical access assembly comprising:
   a valve housing;
   a cannula extending from the valve housing; and
   a valve assembly disposed in the valve housing, the valve assembly including:
      a ring having an opening therethrough and a rim circumscribing the opening;
      a first disc supported on the rim;
      a centering mechanism having a hoop and fingers extending radially from the hoop, the hoop including a ledge in an abutting relationship with the rim;
      a guard with a frame and flaps coupled to the frame, the frame positionable in a channel of the first disc; and
      a seal with a support and petals coupled to the support, the frame and the support abut one another and the first disc is attachable to a second disc irrespective of a rotational orientation of the first disc relative to the second disc.

9. The surgical access assembly of claim 8, wherein the first disc includes a ridge and the second disc includes a slot for receiving the ridge therein.

10. The surgical access assembly of claim 9, wherein the first and second discs are secured to one another.

11. The surgical access assembly of claim 10, wherein the first and second discs are welded together.

12. The surgical access assembly of claim 8, wherein the frame is positionable in the channel such that the guard has a fixed rotational orientation with respect to the first disc.

13. The surgical access assembly of claim 8, wherein the second disc includes a groove adapted to receive the support, the support positionable in the groove such that the seal has a fixed rotational orientation with respect to the second disc.

* * * * *